(12) United States Patent
Johnson et al.

(10) Patent No.: US 7,960,563 B2
(45) Date of Patent: Jun. 14, 2011

(54) INDAZOLES USED TO TREAT ESTROGEN RECEPTOR BETA MEDIATED DISORDERS

(75) Inventors: Christopher Norbert Johnson, Harlow (GB); David G Jones, Durham, NC (US); Xi Liang, Durham, NC (US); David Timothy MacPherson, Harlow (GB); Aaron B Miller, Durham, NC (US); Antoinette Naylor, Harlow (GB); Steven James Stanway, Harlow (GB); Andrew Kenneth Takle, Harlow (GB); Giancarlo Trani, Harlow (GB)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 12/529,561

(22) PCT Filed: Mar. 5, 2008

(86) PCT No.: PCT/EP2008/052664
§ 371 (c)(1),
(2), (4) Date: Sep. 2, 2009

(87) PCT Pub. No.: WO2008/107455
PCT Pub. Date: Sep. 12, 2008

(65) Prior Publication Data
US 2010/0087502 A1    Apr. 8, 2010

(30) Foreign Application Priority Data

Mar. 7, 2007   (GB) .................................. 0704407.6

(51) Int. Cl.
*C07D 231/56* (2006.01)
*A61K 31/416* (2006.01)
(52) U.S. Cl. .................. 548/361.5; 548/361.1; 514/406; 514/407
(58) Field of Classification Search ........................ None
See application file for complete search history.

(56) References Cited

U.S. PATENT DOCUMENTS

| 6,407,261 B1 * | 6/2002 | Anderson et al. ............. 548/440 |
| 2004/0138286 A1 | 7/2004 | Imazaki et al. |
| 2005/0153941 A1 | 7/2005 | Miyabayashi et al. |

FOREIGN PATENT DOCUMENTS

| JP | 07070078 A * | 3/1995 |
| WO | WO 9318008 A1 * | 9/1993 |
| WO | 2006040351 A | 4/2006 |
| WO | WO 2006040351 A1 * | 4/2006 |
| WO | 2007046747 A | 4/2007 |

OTHER PUBLICATIONS

Liu et al. Journal of Organic Chemistry (2008), 73(1), 219-226.*
Mosti, Luisa et al.; 4-substituted 1-phenyl-1H-indazoles with analgesic, antiinflammatory, antipyretic and local anestheic activites; II Farmaco; 1990; 45(4); 415-429; Italy.

* cited by examiner

*Primary Examiner* — Kamal A Saeed
*Assistant Examiner* — Nyeemah Grazier
(74) *Attorney, Agent, or Firm* — J. Scott Young

(57) ABSTRACT

The present invention relates to novel indazole derivatives having pharmacological activity, processes for their preparation, compositions containing them and uses of these compounds in the treatment of estrogen receptor beta mediated diseases.

3 Claims, No Drawings

SEQUENCE LISTING

```
<160> NUMBER OF SEQ ID NOS: 2

<210> SEQ ID NO 1
<211> LENGTH: 284
<212> TYPE: PRT
<213> ORGANISM: Human

<400> SEQUENCE: 1

Met Lys Lys His His His His His Gly Glu Leu Leu Leu Asp Ala
1               5                   10                  15

Leu Ser Pro Glu Gln Leu Val Leu Thr Leu Leu Glu Ala Glu Pro Pro
            20                  25                  30

His Val Leu Ile Ser Arg Pro Ser Ala Pro Phe Thr Glu Ala Ser Met
        35                  40                  45

Met Met Ser Leu Thr Lys Leu Ala Asp Lys Glu Leu Val His Met Ile
    50                  55                  60

Ser Trp Ala Lys Lys Ile Pro Gly Phe Val Glu Leu Ser Leu Phe Asp
65                  70                  75                  80

Gln Val Arg Leu Leu Glu Ser Cys Trp Met Glu Val Leu Met Met Gly
                85                  90                  95

Leu Met Trp Arg Ser Ile Asp His Pro Gly Lys Leu Ile Phe Ala Pro
            100                 105                 110

Asp Leu Val Leu Asp Arg Asp Glu Gly Lys Cys Val Glu Gly Ile Leu
        115                 120                 125

Glu Ile Phe Asp Met Leu Leu Ala Thr Thr Ser Arg Phe Arg Glu Leu
    130                 135                 140

Lys Leu Gln His Lys Glu Tyr Leu Cys Val Lys Ala Met Ile Leu Leu
145                 150                 155                 160

Asn Ser Ser Met Tyr Pro Leu Val Thr Ala Thr Gln Asp Ala Asp Ser
                165                 170                 175

Ser Arg Lys Leu Ala His Leu Leu Asn Ala Val Thr Asp Ala Leu Val
            180                 185                 190

Trp Val Ile Ala Lys Ser Gly Ile Ser Ser Gln Gln Gln Ser Met Arg
        195                 200                 205
```

-continued

Leu Ala Asn Leu Leu Met Leu Leu Ser His Val Arg His Ala Ser Asn
    210                 215                 220

Lys Gly Met Glu His Leu Leu Asn Met Lys Cys Lys Asn Val Val Pro
225                 230                 235                 240

Val Tyr Asp Leu Leu Leu Glu Met Leu Asn Ala His Val Leu Arg Gly
                245                 250                 255

Cys Lys Ser Ser Ile Thr Gly Ser Glu Cys Ser Pro Ala Glu Asp Ser
                260                 265                 270

Lys Ser Lys Glu Gly Ser Gln Asn Pro Gln Ser Gln
    275                 280

<210> SEQ ID NO 2
<211> LENGTH: 275
<212> TYPE: PRT
<213> ORGANISM: Human

<400> SEQUENCE: 2

Met Lys Lys Gly His His His His Gly Leu Val Pro Arg Gly
1               5                   10                  15

Ser Met Ile Lys Arg Ser Lys Lys Asn Ser Leu Ala Leu Ser Leu Thr
                20                  25                  30

Ala Asp Gln Met Val Ser Ala Leu Leu Asp Ala Glu Pro Pro Ile Leu
            35                  40                  45

Tyr Ser Glu Tyr Asp Pro Thr Arg Pro Phe Ser Glu Ala Ser Met Met
        50                  55                  60

Gly Leu Leu Thr Asn Leu Ala Asp Arg Glu Leu Val His Met Ile Asn
65                  70                  75                  80

Trp Ala Lys Arg Val Pro Gly Phe Val Asp Leu Thr Leu His Asp Gln
                85                  90                  95

Val His Leu Leu Glu Cys Ala Trp Leu Glu Ile Leu Met Ile Gly Leu
            100                 105                 110

Val Trp Arg Ser Met Glu His Pro Gly Lys Leu Leu Phe Ala Pro Asn
        115                 120                 125

Leu Leu Leu Asp Arg Asn Gln Gly Lys Cys Val Glu Gly Met Val Glu
    130                 135                 140

Ile Phe Asp Met Leu Leu Ala Thr Ser Ser Arg Phe Arg Met Met Asn
145                 150                 155                 160

Leu Gln Gly Glu Glu Phe Val Cys Leu Lys Ser Ile Ile Leu Leu Asn
                165                 170                 175

Ser Gly Val Tyr Thr Phe Leu Ser Ser Thr Leu Lys Ser Leu Glu Glu
            180                 185                 190

Lys Asp His Ile His Arg Val Leu Asp Lys Ile Thr Asp Thr Leu Ile
        195                 200                 205

His Leu Met Ala Lys Ala Gly Leu Thr Leu Gln Gln Gln His Gln Arg
    210                 215                 220

Leu Ala Gln Leu Leu Leu Ile Leu Ser His Ile Arg His Met Ser Asn
225                 230                 235                 240

Lys Gly Met Glu His Leu Tyr Ser Met Lys Cys Lys Asn Val Val Pro
                245                 250                 255

Leu Tyr Asp Leu Leu Leu Glu Met Leu Asp Ala His Arg Leu His Ala
            260                 265                 270

Pro Thr Ser
    275

INDAZOLES USED TO TREAT ESTROGEN RECEPTOR BETA MEDIATED DISORDERS

CROSS-REFERENCE TO RELATED APPLICATIONS

This application is filed pursuant to 35 USC 371 as a United States National Phase Application of International Patent Application Serial No. PCT/EP2008/052664 filed on Mar. 5, 2008, which claims priority from 0704407.6 filed on Mar. 7, 2007 in the United Kingdom.

FIELD OF THE INVENTION

The present invention relates to novel indazole derivatives having pharmacological activity, processes for their preparation, compositions containing them and uses of these compounds in the treatment of estrogen receptor beta mediated diseases.

BACKGROUND OF THE INVENTION

Estrogens are well-known endocrine regulators in the cellular processes involved in the development and maintenance of the reproductive system. Estrogens have also been shown to have important effects in many non-reproductive tissues such as bone, liver, the cardiovascular system, and the central nervous system. Estrogen receptors are ligand-activated transcription factors and belong to the nuclear hormone receptor subfamily. Upon binding ligand, these receptors dimerize and can activate gene transcription either by directly binding to specific sequences on DNA known as response elements or by interacting with transcription factors (such as API) which in turn bind directly to specific DNA sequences. Additionally, it is now becoming apparent that estrogens may mediate their effects via kinase-mediated signalling cascade, though much of this work is still experimental. Kousteni et al., *Journal of Clinical Investigation*, (2003), 111, 1651-1664.

Historically estrogens were believed to manifest their biological activity through a single estrogen receptor, now termed estrogen receptor alpha (ERα). More recently, however, there was the discovery of second subtype of estrogen receptor, termed estrogen receptor beta (ERβ or ER beta). See, Kuiper et al., WO 97/09348 and Kuiper et al., *Cloning of a Novel Estrogen Receptor Expressed in Rat Prostate and Ovary*, Proc. Natl. Acad. Sci. U.S.A., 1996, pp. 5925-5930. ERβ is expressed in humans. See, Mosselman et al., *ERβ: Identification and Characterization of a Novel Human Estrogen Receptor*, FEBR S Lett., 1996, pp. 49-53. The discovery of this second subtype of estrogen receptor significantly increased the biological complexity of estrogen signalling.

The tissue distribution of ERβ has been well mapped in the rodent and it is not coincident with ERα. Tissues such as the mouse uterus and ovary express predominantly ERα, whereas non reproductive organs e.g. the mouse lung express predominantly ERβ. See Couse, et al., Endocrinology 138: 4613-4621 (1997), Kuiper, et al., Endocrinology 138: 863-870 (1997). Even within the same organ, the distribution of ERα and ERβ can be compartmentalized. For example, in the rat ovary, ERβ is highly expressed in the granulosa cells and ERα is restricted to the thecal and stromal cells. See Sar and Welsch, Endocrinology 140: 963-971 (1999). However, there are examples where the receptors are coexpressed and there is evidence in vitro studies that ERα and ERβ can form heterodimers. See Cowley, et al., Journal of Biological Chemistry 272: 19858-19862 (1997).

The most potent endogenous estrogen is 17β-estradiol. A large number of compounds have been described that either mimic or block the activity of 17β-estradiol. Compounds having roughly the same biological effects as 17β-estradiol are referred to as "estrogen receptor agonists". Those which block the effects of 17β-estradiol, when given in combination with it, are called "estrogen receptor antagonists". In reality, there is a continuum between estrogen receptor agonist and estrogen receptor antagonist activity and some compounds behave as estrogen receptor agonists in some tissues but estrogen receptor antagonists in others. Compounds with mixed activity are called selective estrogen receptor modulators (SERMS) and may be therapeutically useful agents. The precise reason why the same compound can have cell-specific effects has not been elucidated, but the differences in receptor conformation and/or in the milieu of coregulatory proteins have been suggested.

DESCRIPTION OF THE INVENTION

The compounds of the invention bind to the ERβ receptor and may therefore useful in treating ERβ mediated diseases for example the compounds of this invention may be useful in the treatment of pain, chronic inflammatory disorders, autoimmune diseases, CNS disorders, metabolic disorders or appetite disorders. The compounds of the invention may be cardioprotective. The compounds of this invention may also useful in treating or inhibiting benign or malignant abnormal tissue growth, and given that the compounds in this invention are estrogen receptor agonists they may also be useful in the treatment of disorders or conditions at least partially mediated by estrogen deficiency.

The present invention provides, in a first aspect, compounds of formula (I):

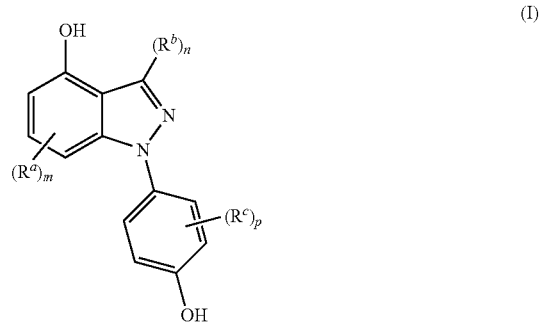

wherein $R^a$, $R^b$ and $R^c$ are independently selected from halo, $C_{1-4}$alkoxy, $C_{1-4}$alkyl, $C_{2-4}$alkenyl, $C_{1-5}$alkanoyl, $CF_3$, $CF_3O$ and cyano, provided that when one of the substitutents is attached to the C-5 of the indazole bicycle, this substituent $R^a$ is not a methoxy group.

m is zero or an integer from 1 to 3;
n is zero or 1;
p is zero or an integer from 1 to 4;
however m, n and p together equal 5 or less;
and pharmaceutically acceptable salts thereof.

In one embodiment, $R^c$ is halo, for example fluoro.
In one embodiment m is zero.
In one embodiment m is 1 and $R^a$ is halo, $C_1$ alkoxy, $C_{1-4}$alkyl, $C_{1-4}$alkenyl or cyano.
In one embodiment $R^c$ is ortho to the hydroxy group on the phenyl ring.

In one embodiment n is zero.

In another embodiment, n is 1 and $R^b$ is a $C_{1-4}$alkyl group

In one embodiment p is zero, 1 or 2.

In one embodiment $R^c$ is F, Cl, or $CH_3$.

Compounds of the invention include the following:

1-(3-Fluoro-4-hydroxyphenyl)-1H-indazol-4-ol;
1-(3-Fluoro-4-hydroxyphenyl)-6-(methyloxy)-1H-indazol-4-ol
1-(3-Fluoro-4-hydroxyphenyl)-4-hydroxy-1H-indazole-6-carbonitrile
6-Fluoro-1-(3-fluoro-4-hydroxyphenyl)-1H-indazol-4-ol
6-Bromo-1-(3-fluoro-4-hydroxyphenyl)-1H-indazol-4-ol
6-Ethenyl-1-(3-fluoro-4-hydroxyphenyl)-1H-indazol-4-ol
6-Ethyl-1-(3-fluoro-4-hydroxyphenyl)-1H-indazol-4-ol
6-Chloro-1-(3-fluoro-4-hydroxyphenyl)-1H-indazol-4-ol
1-(3-Fluoro-4-hydroxyphenyl)-6-methyl-1H-indazol-4-ol
5-Fluoro-1-(3-fluoro-4-hydroxyphenyl)-1H-indazol-4-ol
5-Bromo-1-(3-fluoro-4-hydroxyphenyl)-1H-indazol-4-ol
5-Chloro-1-(3-fluoro-4-hydroxyphenyl)-1H-indazol-4-ol
7-Fluoro-1-(3-fluoro-4-hydroxyphenyl)-1H-indazol-4-ol
7-Chloro-1-(3-fluoro-4-hydroxyphenyl)-1H-indazol-4-ol
1-(3-Fluoro-4-hydroxyphenyl)-3-methyl-1H-indazol-4-ol
1-(4-Hydroxyphenyl)-1H-indazol-4-ol
1-(3-Chloro-4-hydroxyphenyl)-1H-indazol-4-ol
1-(4-hydroxy-3-methylphenyl)-1H-indazol-4-ol
1-(3,5-Difluoro-4-hydroxyphenyl)-1H-indazol-4-ol
1-(3,5-Difluoro-4-hydroxyphenyl)-4-hydroxy-1H-indazole-6-carbonitrile and pharmaceutically acceptable salts thereof.

The term '$C_{1-4}$ alkyl' as used herein as a group or a part of the group refers to a linear or branched saturated hydrocarbon group containing from 1 to 4 carbon atoms. Examples of such groups include methyl, ethyl, n-propyl, isopropyl, n-butyl, isobutyl, sec-butyl and tert-butyl and the like.

The term '$C_{2-4}$ alkenyl' as used herein as a group or a part of the group refers to a linear or branched unsaturated hydrocarbon group containing from 2 to 4 carbon atoms and one double bond. Examples of such groups include ethenyl, 1-prop-2-enyl, 2-prop-2-enyl and the like.

The term '$C_{1-4}$ alkoxy' as used herein refers to an —O—$C_{1-4}$ alkyl group wherein $C_{1-4}$alkyl is as defined herein. Examples of such groups include methoxy, ethoxy, propoxy or butoxy and the like.

The term $C_{1-5}$alkanoyl' as used herein refers to a —C(=O)H or —C(=O)$C_{1-4}$alkyl group wherein $C_{1-4}$alkyl is as defined herein.

The term 'halo' as used herein refers to a fluoro, chloro, bromo or iodo atom.

Compounds of the invention include compounds of formula (I) and pharmaceutically acceptable derivatives thereof which include the compounds of Example 1-20 and pharmaceutically acceptable salts, solvates, hydrates, or solvates or hydrates of a salt thereof, more specifically compounds of Example 1-20 and pharmaceutically acceptable salts thereof.

It is to be understood that the present invention encompasses all isomers of formula (I) and their pharmaceutically acceptable salts, solvates, hydrates, or solvates or hydrates of a salt, including all geometric, tautomeric and optical forms, and mixtures thereof (e.g. racemic mixtures). Where additional chiral centres are present in compounds of formula (I), the present invention includes within its scope all possible diastereoisomers, including mixtures thereof. The different isomeric forms may be separated or resolved one from the other by conventional methods, or any given isomer may be obtained by conventional synthetic methods or by stereospecific or asymmetric syntheses.

The present invention also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine, iodine, and chlorine, such as $^2H$, $^3H$, $^{11}C$, $^{14}C$, $^{18}F$, $^{123}I$ and $^{125}I$.

Compounds of the present invention that contain the aforementioned isotopes and/or other isotopes of other atoms are within the scope of the present invention. Isotopically-labelled compounds of the present invention, for example those into which radioactive isotopes such as $^3H$ and/or $^{14}C$ are incorporated, are useful in drug and/or substrate tissue distribution assays. $^3H$ and $^{14}C$ are considered useful due to their ease of preparation and detectability. $^{11}C$ and $^{18}F$ isotopes are considered useful in PET (positron emission tomography), and $^{125}I$ isotopes are considered useful in SPECT (single photon emission computerized tomography), all useful for in vivo imaging. Substitution with heavier isotopes such as $^2H$ may afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The following definitions are used herein unless otherwise indicated.

The term "pharmaceutically acceptable derivative" means any pharmaceutically acceptable salt, solvate, hydrate or solvate or hydrate of a salt of a compound of formula (I), or any other compound which upon administration to the recipient is capable of providing (directly or indirectly) a compound of formula (I) (e.g. a prodrug).

As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

A further aspect of the invention is Compounds of formula (I) as free acids or bases.

Pharmaceutically acceptable salts include those described by Berge, Bighley and Monkhouse, *J. Pharm. Sci.*, 1977, 66, 1-19. The term "pharmaceutically acceptable salts" refers to salts prepared from pharmaceutically acceptable acids, including inorganic and organic acids or salts prepared from pharmaceutically acceptable bases including inorganic bases and organic bases. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic bases include salts of primary, secondary, and tertiary amines; substituted amines including naturally occurring substituted amines; and cyclic amines. Particular pharmaceutically acceptable organic bases include arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, procaine, purines, theobromine, triethylamine, trimethylamine, tripropylamine, tris(hydroxymethyl)aminomethane (TRIS, trometamol) and the like. Salts may also be formed from basic ion exchange resins, for example polyamine resins. When the compound of the present invention is basic, salts may be prepared from pharmaceutically acceptable acids, including inorganic and organic acids. Such acids include acetic, benzenesulfonic, benzoic, camphorsulfonic, citric, ethanesulfonic, ethanedisulfonic, fumaric, gluconic, glutamic, hydrobromic, hydrochloric, isethionic, lactic, maleic, malic, mandelic, methanesulfonic, mucic, pamoic, pantothenic, phosphoric, propionic, succinic, sulfuric, tartaric, p-toluenesulfonic acid, and the like. In some circumstances some salts may be non-stoichiometric.

The compounds of formula (I) may be prepared in crystalline or non-crystalline form, and may be optionally hydrated or solvated. This invention includes in its scope stoichiometric hydrates as well as compounds containing variable amounts of water.

The compounds of formula (I) may exist in more than one polymorphic form. The invention extends to all such forms whether in a pure polymorphic form or when admixed with any other material, such as another polymorphic form.

Suitable solvates include pharmaceutically acceptable solvates, such as hydrates.

Solvates include stoichiometric solvates and non-stoichiometric solvates.

Compounds of formula (I) can be prepared as set forth in the following Schemes and in the Examples. The following processes form another aspect of the present invention.

Processes for the preparation of a compound of formula (I) comprise;
(a) reaction of a compound of formula (II),

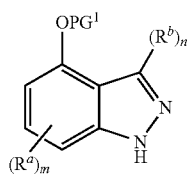

(II)

wherein $R^a$, $R^b$, m and n are as defined for compounds of formula (I) and $PG^1$ represents a protecting group such as methyl or an optionally substituted benzyl group, with a compound of formula (III) or a protected derivative thereof

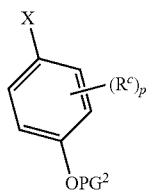

(III)

wherein $R^c$ and p are as defined for compounds of formula (I), $PG^2$ represents a hydrogen or an optional protecting group such as methyl or an optionally substituted benzyl group and X represents a leaving group such as halo (e.g. bromo or iodo) or a residue such as —$B(OH)_2$ or an equivalent boronate ester, and thereafter removing any protecting groups $PG^1$ and $PG^2$;
(b) by reaction of a compound of formula (IV)

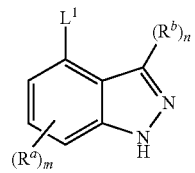

(IV)

wherein $R^a$, $R^b$, m and n are as defined for compounds of formula (I) and $L^1$ represents a leaving group such as a halogen (e.g. bromo), with a compound of formula (III) as defined above, then subsequent reaction with a nucleophile such as hydroxide or the anion derived from a compound of formula $PG^1$-OH (where $PG^1$ is as defined above) in the presence of a suitable transition metal catalyst system (e.g. a mixture of bis(1,1-dimethylethyl)[2',4',6'-tris(1-methylethyl)-2-biphenylyl]phosphane and tris(dibenzylideneacetone)dipalladium (0)) in an appropriate solvent system such as aqueous 1,4-dioxane, followed by removal of protecting groups;
(c) interconversion of a compound of formula (I) or protected derivative thereof;
(d) deprotection of a compound of formula (I) which is protected; and/or
(e) as appropriate, separation of diastereomeric or enantiomeric mixtures of compounds of formula (I) and/or formation of a pharmaceutically acceptable salt, solvate, hydrate, or solvate or hydrate of a salt.

Reactions of compounds of formula (II) with compounds of formula (III) according to process (a) are typically carried out in the presence of a transition metal salt such as a copper halide, an appropriate base such as potassium phosphate, potassium carbonate or triethylamine and, optionally, a suitable coordinating ligand such as a 1,2-diamine (e.g 1,2-(dimethylamino)cyclohexane or an amino acid. Where X represents a leaving group such as halo, use of a copper (I) source is advantageous, such as copper (I) iodide, in the presence of a base such as potassium phosphate or potassium carbonate optionally in the presence of a ligand such as a 1,2-diamine (e.g. 1,2-(dimethylamino)cyclohexane) or an amino acid (e.g. proline). Suitable solvents for this reaction include toluene, dimethylsulfoxide, N,N-dimethylformamide and 1,4-dioxane. Where X represents a residue such as —$B(OH)_2$ or an equivalent boronate ester, a source of copper (II) may be employed, such as copper (II) acetate in the presence of a base such as triethylamine or pyridine advantageously under an oxygen-containing atmosphere such as air using a suitably inert solvent such as dichloromethane. Reactions according to process (a) may be carried out at ambient temperature or elevated temperature e.g. under reflux or using microwave radiation.

In processes (a) and (d), examples of protecting groups and the means for their removal can be found in T. W. Greene 'Protective Groups in Organic Synthesis' (J. Wiley and Sons, 1991). For example an optionally substituted benzyl group may be removed by hydrogenolysis. e.g in the presence of 10% Pd on charcoal.

Separations according to process (e) may be carried out using established methodology, e.g. by chromatography, resolution as diastereomeric salts or crystallisation.

Compounds of formula (II), (III), (IV) are known in the literature or can be purchased from conventional suppliers or can be prepared by conventional methods, e.g. the addition of protecting groups to known compounds, or by methods analogous to those described in the Experimental.

It will be appreciated that compounds of formulas (II), (III) and (IV) may be obtained as mixtures of diastereomers and/or enantiomers. Such mixtures may optionally be separated using established methodology, e.g. by chromatography.

The term "protected derivative thereof" is used herein to refer to compound which includes a protecting group for example those referred to above.

The compounds of the invention bind to the ERβ receptor and may therefore useful in treating ERβ mediated diseases.

In one embodiment compounds of the invention are selective for ERβ over ERα, e.g. in one embodiment compounds of the invention may have greater than 5 fold higher affinity at ERβ compared to ERα.

In view of their ability to bind to the ERβ receptor, the compounds of this invention may be useful in the treatment of the disorders that follow.

The compounds of the formula may be useful in the treatment of pain.

When used herein the term pain, includes acute pain, chronic pain, chronic articular pain, musculoskeletal pain, inflammatory pain, visceral pain, pain associated with cancer, pain associated with migraine, tension headache and cluster headaches, pain associated with functional bowel disorders, lower back and neck pain, pain associated with sprains and strains, sympathetically maintained pain; myositis, pain associated with influenza or other viral infections such as the common cold, pain associated with rheumatic fever, pain associated with myocardial ischemia, post operative pain, headache, toothache and dysmenorrhea.

In one embodiment the compounds may be useful in the treatment of chronic pain, post-operative pain, chronic lower back and neck pain, cancer pain, pain associated with sprains and strains.

Chronic articular pain conditions include rheumatoid arthritis, osteoarthritis, rheumatoid spondylitis, gouty arthritis and juvenile arthritis.

Pain associated with functional bowel disorders includes non-ulcer dyspepsia, non-cardiac chest pain and irritable bowel syndrome.

The compounds of the invention may be also useful in the treatment of chronic inflammatory disorders or autoimmune diseases including arthritis, (rheumatoid, osteoarthritis and spondyloarthropathies), inflammatory bowel disease (Crohn's disease, ulcerative colitis, indeterminate colitis), multiple sclerosis, diabetes, ischemia/reperfusion injury, psoriasis, sepsis, systemic lupus erythematosus and endometriosis.

The compounds of the invention may be cardioprotective and useful for the treatment of hypercholesteremia, atherosclerosis, cardiovascular disease, hyperlipidemia and immune cell mediated vascular damage.

The compounds of the invention may also be useful in treating benign or malignant abnormal tissue growth including prostatic hypertrophy, breast cancer, colon cancer and prostate cancer.

Compounds exhibiting ERβ receptor binding activity have been described to have activity in brain and therefore may be useful for inhibiting or treating CNS disorders including depression, anxiety, insomnia, schizophrenia, Alzheimer's disease, cognitive decline, senile dementia and neurodegenerative disorders.

As compounds of the invention are estrogen receptor agonists they may be useful in the treatment of disorders or conditions at least partially mediated by estrogen deficiency. In particular, these compounds may be useful for the treatment of menopausal and post-menopausal disorders (vasomotor symptoms, urogenital or vulvar vaginal atrophy, atrophic vaginitis, female sexual dysfunction, bone demineralization and the treatment of osteoporosis.

Additional indications include metabolic disorders such as type II diabetes and appetite disorders (obesity).

When used herein the term "treatment" extends to prophylaxis of the above disorders as well as treatment of established conditions, e.g. inhibition of benign or malignant abnormal tissue, prophylaxis of menopausal and post-menopausal disorders, osteoporosis and osteoarthritis or protection against a cardio event (cardio protection).

Thus the invention also provides a compound of formula (I) or a pharmaceutically acceptable salt solvate, hydrate, or solvate or hydrate of a salt thereof, for use as a cardioprotective therapy or as a therapeutic substance in the treatment of the above disorders, in particular pain, chronic inflammatory disorders, autoimmune diseases, benign or malignant abnormal tissue growth, CNS disorders, metabolic disorders, appetite disorders, disorders or conditions at least partially mediated by estrogen deficiency.

The invention further provides a method of treatment of the above disorders, in mammals including humans, which comprises administering to the sufferer a therapeutically effective amount of a compound of formula (I) or a pharmaceutically acceptable salt, solvate, hydrate, or solvate or hydrate of a salt thereof.

In another aspect, the invention provides the use of a compound of formula (I) or a pharmaceutically acceptable salt, solvate, hydrate, or solvate or hydrate of a salt thereof in the manufacture of a medicament for use in the treatment of the above disorders.

When used in therapy, the compounds of formula (I) are usually formulated in a standard pharmaceutical composition. Such compositions can be prepared using standard procedures.

Thus, the present invention further provides a pharmaceutical composition for use in the treatment of the above disorders which comprises the compound of formula (I) or a pharmaceutically acceptable salt, solvate, hydrate, or solvate or hydrate of a salt thereof and a pharmaceutically acceptable carrier.

The present invention further provides a pharmaceutical composition which comprises the compound of formula (I) or a pharmaceutically acceptable salt, solvate, hydrate, or solvate or hydrate of a salt thereof and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusible solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colorants.

For parenteral administration, fluid unit dosage forms may be prepared utilising a compound of the invention or pharmaceutically acceptable salt, solvate, hydrate, or solvate or hydrate of a salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilisation cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.01% to 99% by weight, preferably from 1 to 60% by weight, of the active material, depending on the method of administration. The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 1.0 to 200 mg, and such unit doses may be administered more than once a day, for example two or three a day. Such therapy may extend for a number of weeks or months.

A further aspect to the invention is a pharmaceutical composition comprising 0.05 to 1000 mg of a compound of formula (I) or a pharmaceutically acceptable salt, solvate, hydrate, or solvate or hydrate of a salt thereof, and 0 to 3 g more suitably 0 to 2 g of at least one pharmaceutically acceptable carrier, e.g. a binding agent, a filler, a tableting lubricant, a disintegrant and or a wetting agent.

The precise amount of the compounds of formula (I) administered to a host, particularly a human patient, will be the responsibility of the attendant physician. However, the dose employed will depend on a number of factors including the age and sex of the patient, the precise condition being treated and its severity, and the route of administration.

Compounds of formula (I) or a pharmaceutically acceptable salt, solvate, hydrate, or solvate or hydrate of a salt thereof may be used in combination with other therapeutic agents.

The compounds of the invention may be used in combination with other therapeutic agents, for example COX-2 (cyclooxygenase-2) inhibitors, such as celecoxib, deracoxib, rofecoxib, valdecoxib, parecoxib, COX-189 or 2-(4-ethoxyphenyl)-3-(4-methanesulfonyl-phenyl)-pyrazolo[1,5-b]pyridazine (WO99/012930); 5-lipoxygenase inhibitors; NSAIDs (non-steroidal anti-inflammatory drugs) such as diclofenac, indomethacin, nabumetone or ibuprofen; bisposphates, leukotriene receptor antagonists; DMARDs (disease modifying anti-rheumatic drugs) such as methotrexate; adenosine A1 receptor agonists; sodium channel blockers, such as lamotrigine; NMDA (N-methyl-D-aspartate) receptor modulators, such as glycine receptor antagonists; ligands for the $\alpha_2\delta$-subunit of voltage gated calcium channels, such as gabapentin and pregabalin; tricyclic antidepressants such as amitriptyline; neurone stabilising antiepileptic drugs; mono-aminergic uptake inhibitors such as venlafaxine; opioid analgesics; local anaesthetics; 5HT$_1$ agonists, such as triptans, for example sumatriptan, naratriptan, zolmitriptan, eletriptan, frovatriptan, almotriptan or rizatriptan; nicotinic acetyl choline (nACh) receptor modulators; glutamate receptor modulators, for example modulators of the NR2B subtype; EP$_4$ receptor ligands; EP$_2$ receptor ligands; EP$_3$ receptor ligands; EP$_4$ agonists and EP$_2$ agonists; EP$_4$ antagonists; EP$_2$ antagonists and EP$_3$ antagonists; cannabanoid receptor ligands; bradykinin receptor ligands; vanilloid receptor ligand; and purinergic receptor ligands, including antagonists at P2X$_3$, P2X$_{2/3}$, P2X$_4$, P2X$_7$ or P2X$_{4/7}$. When the compounds are used in combination with other therapeutic agents, the compounds may be administered either sequentially or simultaneously by any convenient route.

Additional COX-2 inhibitors are disclosed in U.S. Pat. No. 5,474,995 U.S. Pat. No. 5,633,272; U.S. Pat. No. 5,466,823, U.S. Pat. No. 6,310,099 and U.S. Pat. No. 6,291,523; and in WO 96/25405, WO 97/38986, WO 98/03484, WO 97/14691, WO99/12930, WO00/26216, WO00/52008, WO00/38311, WO01/58881 and WO02/18374.

Other therapeutic agents claimed to be useful as either disease modifying or symptomatic treatments of Alzheimer's disease may be used in combination with the compounds of the present invention. Suitable examples of such other therapeutic agents may be agents known to modify cholinergic transmission such as 5-HT$_{1A}$ antagonists, (e.g. lecozotan), 5-HT6 antagonists, M1 muscarinic agonists, M2 muscarinic antagonist, acetylcholinesterase inhibitors (e.g donepezil or rivastigmine), or allosteric modulators, nicotinic receptor agonists or allosteric modulators, symptomatic agents such as 5-HT6 receptor antagonists, e.g. SB742457, H3 receptor antagonists e.g. GSK189254 and GSK239512, 5HT4 receptor agonist, also NMDA receptor antagonists or modulators, and PPARγ modulators, and disease modifying agents such as β or γ-secretase inhibitors and/or modulators (e.g. R-flurbiprofen). Other suitable examples of such other therapeutic agents may be medicaments claimed to be useful in the treatment of pain of neuropathic origin including neuralgias, neuritis and back pain, and inflammatory pain including osteoarthritis, rheumatoid arthritis, acute inflammatory pain, back pain and migraine.

When the compounds are used in combination with other therapeutic agents, the compounds may be administered either sequentially or simultaneously by any convenient route.

The invention thus provides, in a further aspect, a combination comprising a compound of formula (I) or a pharmaceutically acceptable salt, solvate, hydrate, or solvate or hydrate of a salt thereof together with a further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of formula (I) or a pharmaceutically acceptable salt, solvate, hydrate, or solvate or hydrate of a salt thereof is used in combination with a second therapeutic agent active against the same disease state the dose of each compound may differ from that when the compound is used alone. Appropriate doses will be readily appreciated by those skilled in the art.

All publications, including but not limited to patents and patent applications, cited in this specification are herein incorporated by reference as if each individual publication were specifically and individually indicated to be incorporated by reference herein as though fully set forth.

The following non-limiting Examples illustrate the preparation of pharmacologically active compounds of the invention.

EXAMPLES

In the procedures that follow, after each starting material, reference to a description is typically provided. This is provided merely for assistance to the skilled chemist. The starting material may not necessarily have been prepared as described in the description referred to.

LC/Mass spectra were obtained using either a
5 minute method

Agilent 1100 series HPLC system coupled with a Waters ZQ Mass Spectrometer. LC analysis was performed on a Waters Atlantis column (50×4.6 mm, 3 μm) (mobile phase: 97% [water+0.05% HCO₂H]/3% [CH₃CN+0.05% HCO₂H] for 0.1 min, then a gradient to 3% [water+0.05% HCO₂H]/ 97% [CH₃CN+0.05% HCO₂H] over 3.9 min, and then held under these conditions for 0.8 min); temperature=30° C.; flow rate=3 mL/min; Mass spectra were collected using electrospray and/or APCI. In the mass spectra only one peak in the molecular ion cluster is reported. The UV detection range is from 220 to 330 nm.

Or a 2 minute method

Hardware: Waters Acquity Binary solvent Manager, Waters Acquity Sample Manager, Waters Acquity Column Oven, Waters Acquity Photo Diode Array, Waters ZQ Mass Spectrometer, Polymer Labs ELSD PL1000, Computer System. XP SP2

Software: Waters MassLynx v4.1

Column: Acquity HPLC BEH $C_{18}$ 1.7 μm 2.1 mm×50 mm, column oven set to 40 degrees centigrade Solvents: A—Aqueous solvent=Water 0.1% Formic Acid+ 10 mM Ammonium Acetate, B—Organic solvent=MeCN: Water 95:5+0.05% Formic Acid Instrument settings: Injection volume: 0.5 μl, UV detection: 220 to 330 nm, MS scan range: 100 to 1000 amu, MS scanning rate: 0.2 second scan with a 0.1 second inter scan delay, MS scan function: Electrospray with pos neg switching Gradient:

| Time | Flow mL/min | % A | % B |
|------|-------------|-----|-----|
| 0    | 1           | 97  | 3   |
| 0.1  | 1           | 97  | 3   |
| 1.4  | 1           | 0   | 100 |
| 1.9  | 1           | 0   | 100 |
| 2    | 1           | 97  | 3   |

Proton Magnetic Resonance (NMR) spectra were recorded on a Bruker instrument at 250 or 400 MHz. Chemical shifts are reported in ppm (δ) using tetramethylsilane as internal standard. Splitting patterns are designated as s, singlet; d, doublet; t, triplet; q, quartet; m, multiplet; br, broad. The NMR spectra were recorded at a temperature ranging from 25 to 90° C. When more than one conformer was detected the chemical shifts for the most abundant one are reported.

Chromatography was carried out on silica gel cartridges either on a Flashmaster II (Argonaut) or a Biotage SP4 automated chromatography system and an appropriate elution solvent system.

Mass Directed Automated Preparative (MDAP) HPLC instruments consist of the following: Waters 2525 Binary Gradient Module, Waters 515 Makeup Pump, Waters Pump Control Module, Waters 2767 Inject Collect, Waters Column Fluidics Manager, Waters 2996 Photodiode Array Detector, Waters ZQ Mass Spectrometer, Gilson 202 fraction collector, Gilson Aspec waste collector. Column: Waters Atlantis, dimensions are 19 mm×100 mm (<100 mg scale) and 30 mm×100 mm (>100 mg scale), particle size is 5 μm. Solvents, A: Aqueous solvent=Water+0.1% Formic Acid B: Organic solvent=Acetonitrile+0.1% Formic Acid. Gradients range from 5-30% B in A to 80-99% B in A, depending on HPLC retention time, run time=13.5 minutes. Flow rate=20 mL/min (<100 mg scale), 40 mL/min (>100 mg scale)

The H-Cube™ is a continuous flow hydrogenation instrument manufactured by THALES Inc (Budapest)

Abbreviations used herein are
DMF—N,N-Dimethylformamide
DCM—Dichloromethyl
THF—Tetrahydrofuran DME—Ethylene glycol dimethyl ether
Pd₂ dba₃—Tris(dibenzylideneacetone)dipalladium (0)

Description 1

4-[(Phenylmethyl)oxy]-1H-indazole (D1)

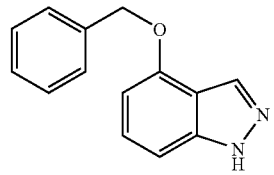

To a stirred solution of 4-hydroxyindazole (702 mg, 5.24 mmol) in DMF (10 mL) at ambient temperature under argon was added sodium hydride (231 mg of a 60% dispersion in mineral oil, 5.76 mmol). The mixture was stirred for 10 minutes and then benzyl bromide (0.622 mL, 5.24 mmol) was added via syringe. After stirring for 2 hours at ambient temperature, the mixture was quenched with ammonium chloride solution, the solvents were evaporated and ethyl acetate and water were added. The product was extracted into ethyl acetate and the organic solution was dried (Na₂SO₄) and evaporated.

Chromatography (silica gel, elution with 0-100% ethyl acetate in hexane) gave the title compound (D1) (0.532 g).

LC-MS: MH⁺=225 ($C_{14}H_{12}N_2O$=224)

Description 2

1-{3-Fluoro-4-[(phenylmethyl)oxy]phenyl}-4-[(phenylmethyl)oxy]-1H-indazole (D2)

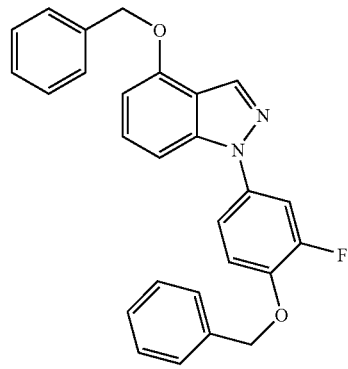

A mixture of 4-[(phenylmethyl)oxy]-1H-indazole (D1) (530 mg, 2.37 mmol), {3-fluoro-4-[(phenylmethyl)oxy] phenyl}boronic acid (873 mg, 3.55 mmol), copper acetate (861 mg, 4.74 mmol), triethylamine (0.660 mL, 4.74 mmol) and powdered 4A molecular sieves (2.5 g) in dichloromethane (10 mL) was stirred vigorously under an air atmosphere at ambient temperature. Further quantities of boronic acid, triethylamine and copper acetate were added after 18 hours (0.5 equivalents of each) and 22 hours (1 equivalent of each). After stirring for a further 24 hrs, the mixture was filtered through a plug of silica gel and concentrated. Chromatography (silica gel, elution with 0-20% ethyl acetate in hexane) gave the title compound (D2) as a white solid (309 mg).

LC-MS: MH⁺=425 ($C_{27}H_{21}FN_2O_2$=347)

Description 3

4-Bromo-1-{3-fluoro-4-[(phenylmethyl)oxy]phenyl}-6-(methyloxy)-1H-indazole (D3)

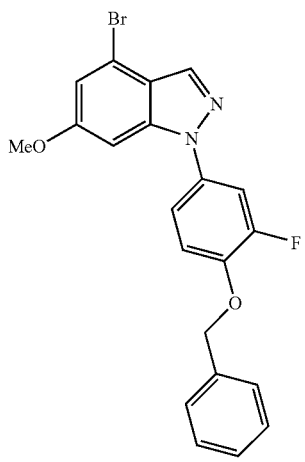

To a solution of 4-bromo-6-(methyloxy)-1H-indazole (200 mg, 0.88 mmol) in dichloromethane (10 mL) was added 4-benzyloxy-3-fluorobenzeneboronic acid (433 mg, 1.76 mmol), pyridine (0.14 mL, 1.73 mmol), copper acetate (239 mg, 1.32 mmol) and powdered 4A molecular sieves (500 mg). The reaction mixture was stirred at room temperature in the presence of air for 3 days. Celite was added to the mixture then the mixture was filtered through a pad of celite and then the filtrate concentrated in vacuo. The product was purified by silica gel chromatography eluting with 5-80% dichloromethane in hexane to yield the title compound (D3) (176 mg).

LC-MS: MH$^+$=427, 429 ($C_{21}H_{16}BrFN_2O_2$=426, 428)

Description 4

1-{3-Fluoro-4-[(phenylmethyl)oxy]phenyl}-6-(methyloxy)-1H-indazol-4-ol (D4)

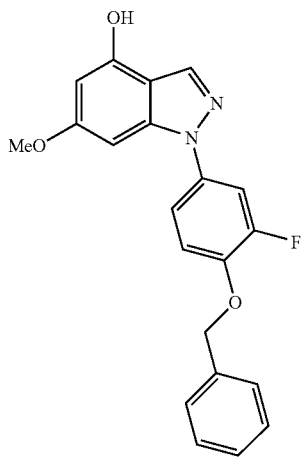

To a solution of 4-bromo-1-{3-fluoro-4-[(phenylmethyl)oxy]phenyl}-6-(methyloxy)-1H-indazole (D3) (176 mg, 0.41 mmol) in dioxane (5 mL) and water (5 mL) was added potassium hydroxide (92 mg, 1.64 mmol). The reaction mixture was degassed with argon and then treated with bis(1,1-dimethylethyl)[2',4',6'-tris(1-methylethyl)-2-biphenylyl]phosphane (10 mg, 0.02 mmol) and tris(dibenzylideneacetone)dipalladium (0) (8 mg, 0.009 mmol). After heating at 90° C. for 1 hour, the mixture was allowed to cool to room temperature and then diluted with ethyl acetate and water. The pH was adjusted to 7 by the addition of 1M hydrochloric acid. After separation of the layers, the aqueous phase was re-extracted with ethyl acetate. The combined organic layers were dried over magnesium sulphate, filtered and concentrated in vacuo. The product was purified by silica gel chromatography eluting with 5-70% ethyl acetate in hexane to yield the title compound (D4) (118 mg).

LC-MS: MH$^+$=365 ($C_{21}H_{17}FN_2O_3$=364)

Description 5

4-Bromo-1-{3-fluoro-4-[(phenylmethyl)oxy]phenyl}-1H-indazole-6-carbonitrile (D5)

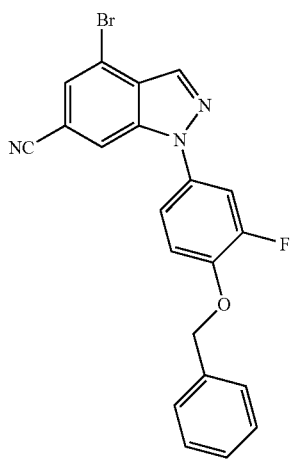

To a solution of 4-bromo-1H-indazole-6-carbonitrile (1.0 g, 4.50 mmol) in dichloromethane (80 mL) was added 4-benzyloxy-3-fluorobenzeneboronic acid (2.2 g, 8.94 mmol), pyridine (0.71 mL, 8.78 mmol), copper acetate (1.2 g, 6.63 mmol) and powdered 4A molecular sieves (2.0 g). The reaction mixture was stirred at room temperature in the presence of air for 6 days. Celite was added to the mixture then the mixture was filtered through a pad of celite and then the filtrate concentrated in vacuo. The product was purified by silica gel chromatography eluting with 5-100% dichloromethane in hexane to yield the title compound (D5) (774 mg).

LC-MS: MH$^+$=422, 424 ($C_{21}H_{13}BrFN_3O$=421, 423)

Description 6

1-{3-Fluoro-4-[(phenylmethyl)oxy]phenyl}-4-hydroxy-1H-indazole-6-carbonitrile (D6)

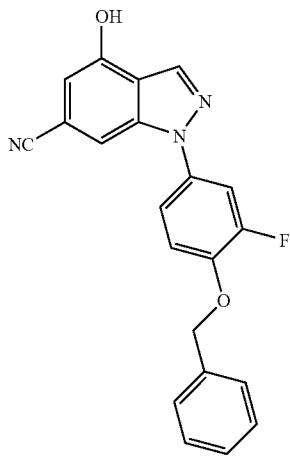

To a solution of 4-bromo-1-{3-fluoro-4-[(phenylmethyl)oxy]phenyl}-1H-indazole-6-carbonitrile (D5) (535 mg, 1.27 mmol) in dioxane (10 mL) and water (10 mL) was added potassium hydroxide (284 mg, 5.07 mmol). The reaction mixture was degassed with argon and then treated with bis(1,1-dimethylethyl)[2',4',6'-tris(1-methylethyl)-2-biphenylyl]phosphane (32 mg, 0.075 mmol) and tris(dibenzylideneacetone)dipalladium (0) (23 mg, 0.025 mmol). After heating at 90° C. for 1 hour, the mixture was allowed to cool to room temperature and then diluted with ethyl acetate and water. The pH was adjusted to 7 by the addition of 1M hydrochloric acid. After separation of the layers, the aqueous phase was re-extracted with ethyl acetate. The combined organic layers were dried over magnesium sulphate, filtered and concentrated in vacuo. The product was purified by silica gel chromatography eluting with 5-100% ethyl acetate in hexane to yield the title compound (D6) (308 mg).

LC-MS: MH$^+$=360 (C$_{21}$H$_{14}$FN$_3$O$_2$=359)

Description 7

4-Bromo-6-fluoro-1-{3-fluoro-4-[(phenylmethyl)oxy]phenyl}-1H-indazole (D7)

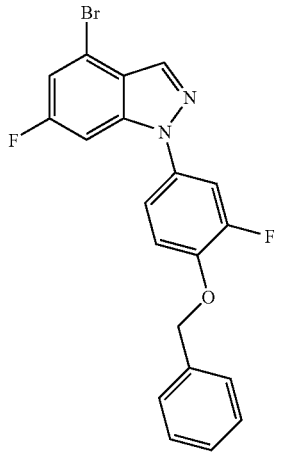

To a solution of 4-bromo-6-fluoro-1H-indazole (1.0 g, 4.65 mmol) in dichloromethane (50 mL) was added 4-benzyloxy-3-fluorobenzeneboronic acid (2.29 g, 9.31 mmol), pyridine (0.75 mL, 9.28 mmol), copper acetate (1.26 g, 6.96 mmol) and powdered 4A molecular sieves (2 g). The reaction mixture was stirred at room temperature in the presence of air for 4 days. Celite was added to the mixture and stirred for 5 mins, then the mixture was filtered through a pad of celite and then the filtrate was washed with water, dried over magnesium sulphate, filtered and concentrated. The product was purified by silica gel chromatography eluting with 5-100% dichloromethane in hexane to yield the title compound (D7) (779 mg).

LC-MS: MH$^+$=415, 417 (C$_{20}$H$_{13}$BrF$_2$N$_2$O=414, 416)

Description 8

6-Fluoro-1-{3-fluoro-4-[(phenylmethyl)oxy]phenyl}-1H-indazol-4-ol (D8)

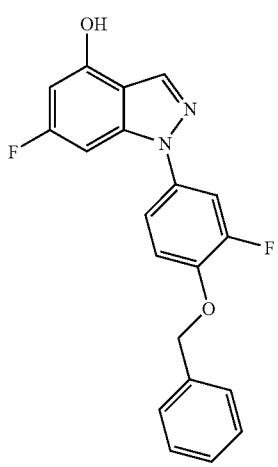

To a solution of 4-bromo-6-fluoro-1-{3-fluoro-4-[(phenylmethyl)oxy]phenyl}-1H-indazole (D7) (670 mg, 1.61 mmol) in dioxane (20 mL) and water (20 mL) was added potassium hydroxide (362 mg, 6.46 mmol). The reaction mixture was degassed with argon and then treated with bis(1,1-dimethylethyl)[2',4',6'-tris(1-methylethyl)-2-biphenylyl]phosphane (41 mg, 0.097 mmol) and tris(dibenzylideneacetone)dipalladium (0) (30 mg, 0.033 mmol). After heating at 90° C. for 1 hour, the mixture was allowed to cool to room temperature and then diluted with ethyl acetate and water. The pH was adjusted to 7 by the addition of 1M hydrochloric acid. After separation of the layers, the aqueous phase was re-extracted with ethyl acetate. The combined organic layers were dried over magnesium sulphate, filtered and concentrated in vacuo. The product was purified by silica gel chromatography eluting with 5-80% ethyl acetate in hexane to yield the title compound (D8) (473 mg).

LC-MS: MH$^+$=353 (C$_{20}$H$_{14}$F$_2$N$_2$O$_2$=352)

Description 9

6-Bromo-1-{3-fluoro-4-[(phenylmethyl)oxy]phenyl}-4-(methyloxy)-1H-indazole (D9)

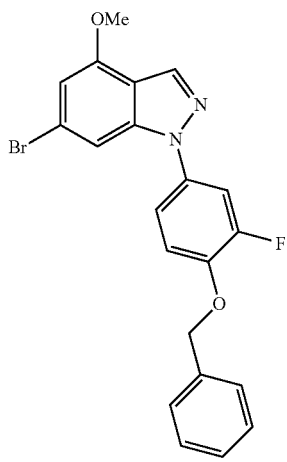

To a solution of 6-bromo-4-(methyloxy)-1H-indazole (1.0 g, 4.40 mmol) in dichloromethane (50 mL) was added 4-benzyloxy-3-fluorobenzeneboronic acid (2.16 g, 8.80 mmol), pyridine (0.71 mL, 8.79 mmol), copper acetate (1.2 g, 6.62 mmol) and powdered 4A molecular sieves (2 g). The reaction mixture was stirred at room temperature in the presence of air for 5 days. Celite was added to the mixture and stirred for 10 mins then the mixture was filtered through a pad of celite and then the filtrate was washed with dichloromethane, then washed with water, dried over magnesium sulphate, filtered and concentrated. The product was purified by silica gel chromatography eluting with 5-30% ethyl acetate in hexane to yield the title compound (D9) (1.23 g).

LC-MS: MH$^+$=427, 429 ($C_{21}H_{16}BrFN_2O_2$=426, 428)

Description 10

4-Bromo-6-chloro-1-{3-fluoro-4-[(phenylmethyl)oxy]phenyl}-1H-indazole (D10)

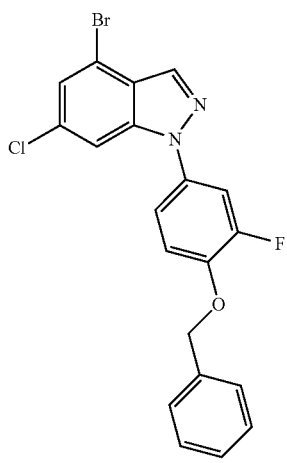

4-Bromo-6-chloro-1H-indazole (413 mg, 1.78 mmol), {3-fluoro-4-[(phenylmethyl)oxy]phenyl}boronic acid (876 mg, 3.56 mmol), copper (II) acetate (483 mg, 2.67 mmol) and pyridine (0.29 mL, 3.56 mmol) in DCM (30 mL) were stirred in the presence of molecular sieves (4A, 790 mg) in air. After 40 hours the mixture was filtered through a pad of celite and concentrated to afford 1.24 g of crude material. This was purified by flash chromatography (Biotage SP4, 40+M silica column) with a gradient of Et$_2$O (0 to 30%) in hexane to afford 410 mg of desired compound (D10) containing a small amount of the N2-aryl regioisomer.

LC-MS: MH$^+$=432 ($C_{20}H_{13}BrClFN_2O$=431)

Description 11

6-Chloro-1-{3-fluoro-4-[(phenylmethyl)oxy]phenyl}-1H-indazol-4-ol (D11)

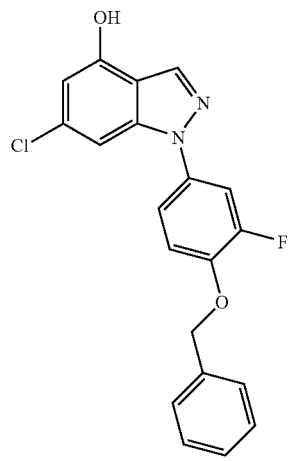

A solution of 4-bromo-6-chloro-1-{3-fluoro-4-[(phenylmethyl)oxy]phenyl}-1H-indazole (D10) (410 mg, 0.95 mmol) and KOH (212 mg, 3.8 mmol) in dioxane (10 mL) and water (10 mL) was sonicated under a flow of argon for 5 minutes after which the bis(1,1-dimethylethyl)[2',4',6'-tris(1-methylethyl)-2-biphenylyl]phosphane (24 mg, 0.057 mmol) and Pd$_2$dba$_3$ (17 mg, 0.019 mmol) were added and it was heated to reflux for 2 hours. The mixture was then cooled to room temperature, diluted with EtOAc and water and the pH was adjusted to circa 7. The phases were separated, the aqueous re-extracted with EtOAc and the combined organics were finally dried over MgSO$_4$. The crude material (450 mg) was purified by flash chromatography (Biotage SP4, 25+M silica column) with a gradient of EtOAc 0 to 50% in hexane to afford 60 mg of desired compound (D11).

LC-MS: MH$^+$=369 ($C_{20}H_{14}ClFN_2O_2$=368)

Description 12

4-Bromo-1-{3-fluoro-4-[(phenylmethyl)oxy]phenyl}-6-methyl-1H-indazole (D12)

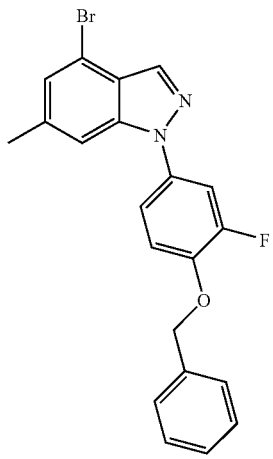

The 4-bromo-6-methyl-1H-indazole (950 mg, 4.5 mmol), the {3-fluoro-4-[(phenylmethyl)oxy]phenyl}boronic acid (2.2 g, 9 mmol), copper (II) acetate (1.22 g, 6.75 mmol) and pyridine (0.73 mL, 9 mmol) in DCM (80 mL) were stirred in the presence of molecular sieves (4 A, 2 g) in air. After 40 hours the mixture was filtered through a pad of celite and concentrated to afford 3.3 g of crude material. This was purified by flash chromatography (Biotage SP4, 40+M silica column) with a gradient of EtOAc 0 to 30% in hexane to afford 1.98 g of desired compound (D12) slightly impure but carried forward.

LC-MS: MH$^+$=412 (C$_{21}$H$_{16}$BrFN$_2$O=411)

Description 13

1-{3-Fluoro-4-[(phenylmethyl)oxy]phenyl}-6-methyl-1H-indazol-4-ol (D13)

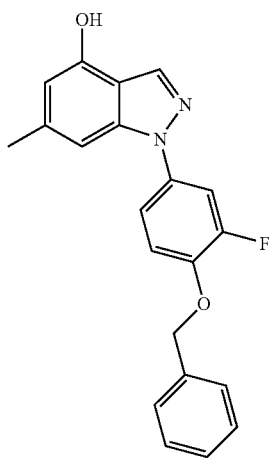

A solution of 4-bromo-1-{3-fluoro-4-[(phenylmethyl)oxy]phenyl}-6-methyl-1H-indazole (D12) (1.97 g, 4.5 mmol) and KOH (1 g, 18 mmol) in dioxane (50 mL) and water (50 mL) was sonicated under a flow of argon for 5 minutes after which the bis(1,1-dimethylethyl)[2',4',6'-tris(1-methylethyl)-2-biphenylyl]phosphane (115 mg, 0.27 mmol) and Pd$_2$dba$_3$ (82 mg, 0.09 mmol) were added and it was heated to reflux for 2 hours. The mixture was then cooled to room temperature, diluted with EtOAc and water and the pH was adjusted to circa 7 with 1M HCl. The phases were separated, the aqueous re-extracted with EtOAc and the combined organics were finally dried over MgSO$_4$. The crude material (2.1 g) was purified by flash chromatography (Biotage SP4, 40+M silica column) with a gradient of EtOAc 0 to 50% in hexane to afford 730 mg of desired compound (D13).

LC-MS: MH$^+$=349 (C$_{21}$H$_{17}$FN$_2$O$_2$=348)

Description 14

2-Bromo-3,6-difluorobenzaldehyde (D14)

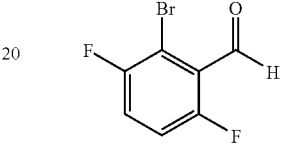

To solution of diisopropylamine (13.29 mL, 93 mmol) in THF (300 mL) at −78° C., was added n-butyllithium (34.2 mL of 2.5M in hexanes, 85 mmol), dropwise over 10 mins. The mixture was stirred at −78° C. for 15 mins and then 2-bromo-1,4-difluorobenzene (15 g, 78 mmol) in THF (100 mL) was added dropwise over 15 mins maintaining the temperature below −65° C. After stirring for 1 hr at −78° C., N,N-dimethylformamide (6.62 mL, 85 mmol) was added via syringe. The mixture was stirred at −78° C. for 30 mins and then quenched with sat. NH$_4$Cl solution and the mixture was allowed to reach room temperature. The product was extracted into ether and the extracts were dried (Na$_2$SO$_4$) and evaporated. Chromatography (silica, 0-100% dichloromethane in hexane) gave the title compound (D14) as a yellow solid (12.73 g)

NMR (δ$_H$), (CDCl$_3$): 7.16 (1H, m), 7.35 (1H, m), 10.32 (1H, s).

Description 15

4-Bromo-5-fluoro-1H-indazole (D15)

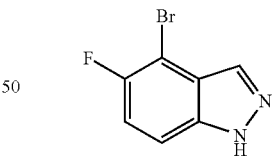

To a solution of 2-bromo-3,6-difluorobenzaldehyde (D14) (6 g, 27.1 mmol) in 1,2-dimethoxyethane (25 mL) was added hydrazine monohydrate (30 mL, 956 mmol) over 5 mins. The mixture was then refluxed under argon for 6 days. The solution was evaporated down to ~10 mL and the mixture was poured into water (500 mL). The precipitated solid was collected by filtration, washed with water (3×) and dried to give 1.4 g of crude product. The aqueous was extracted with ethyl acetate (2×), and the extracts were dried over Na$_2$SO$_4$ and evaporated to give another 0.4 g solid which was combined with the earlier batch and chromatographed (silica gel, ethyl acetate in hexane) to give the title compound (D15) as a white solid (1.01 g)

LC-MS: MH$^+$=215/217 (C$_7$H$_4$BrFN$_2$=214/216).

Description 16

4-Bromo-5-fluoro-1-{3-fluoro-4-[(phenylmethyl)oxy]phenyl}-1H-indazole (D16)

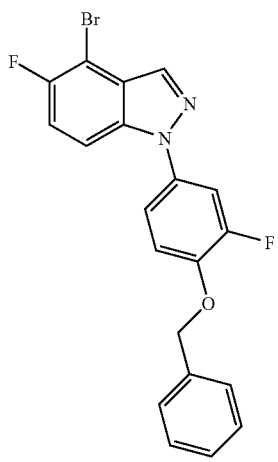

A mixture of 4-bromo-5-fluoro-1H-indazole (D15) (1.008 g, 4.69 mmol), {3-fluoro-4-[(phenylmethyl)oxy]phenyl}boronic acid 1.730 g, 7.03 mmol), copper(II) acetate (1.277 g, 7.03 mmol) and pyridine (0.758 mL, 0.742 g, 9.38 mmol) were stirred together vigorously under an air atmosphere with powdered 4A molecular sieves (5 g) at room temperature. After 6 days another 580 mg of boronic acid were added and stirring continued for a further 24 hrs. The mixture was filtered through celite, the celite was washed with dichloromethane and the combined filtrate was washed with water, dried over $Na_2SO_4$ and evaporated. Chromatography (silica gel, 0-100% dichloromethane in isohexane), followed by trituration of the product with diethyl ether gave the title compound (D16) (0.968 g) as a white solid.

LC-MS: $MH^+$=415/417 ($C_{20}H_{13}BrFN_2O$=414/416)

Description 17

5-Fluoro-1-{3-fluoro-4-[(phenylmethyl)oxy]phenyl}-1H-indazol-4-ol (D17)

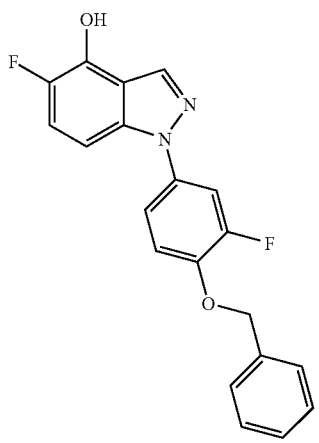

A suspension of 4-bromo-5-fluoro-1-{3-fluoro-4-[(phenylmethyl)oxy]phenyl}-1H-indazole (D16) (0.968 g, 2.331 mmol) in 1,4-dioxane (20 mL)/water (20 mL) was stirred and treated with potassium hydroxide (0.523 g, 9.32 mmol), $Pd_2dba_3$ (42.7 mg, 0.047 mmol) and 2-di-tertbutylphosphino-2',4',6'-triisopropylbiphenyl (59.4 mg, 0.140 mmol) and the mixture was refluxed under argon. After refluxing for 6 hrs the same quantities of $Pd_2dba_3$ and 2-di-tertbutylphosphino-2',4',6'-triisopropylbiphenyl were added and refluxing continued for a further 3 hrs. The mixture was diluted with water/ethyl acetate and the pH was adjusted to 6 with 2M HCl. The product was extracted into ethyl acetate and the extracts were dried ($Na_2SO_4$) and concentrated.

Chromatography (silica, dichloromethane/hexane) gave the title compound (D17) as a beige solid (0.612 g)

LC-MS: $MH^+$=353 ($C_{20}H_{14}F_2N_2O_2$=352)

Description 18

3-Bromo-6-fluoro-2-(methyloxy)benzaldehyde (D18)

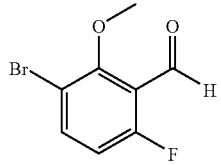

To a solution of diisopropylamine (6.89 g, 9.6 mL, 68.3 mmol) in THF (100 mL) at −78° C. was added n-butyl lithium (33.5 mL of 1.6 M solution in hexane, 53.6 mmol) over 3 mins. After stirring at −78° C. for 10 mins, 2-bromo-5-fluoroanisole (10 g, 48.8 mmol) in THF (20 mL) was added dropwise over 15 mins. After completion of the addition, the mixture was stirred at −78° C. for 1 hr and then DMF (3.91 g, 4.12 mL, 53.6 mmol) was added dropwise over 3 mins and stirring was continued at −78° C. for 45 mins. Saturated $NH_4Cl$ solution was added and the mixture allowed to each room temperature. Diethyl ether and 2M HCl were added, the product was extracted into diethyl ether and the combined extracts were washed with brine, dried and evaporated. Chromatography on silica gel followed by trituration of the product with diethyl ether gave the title compound (D18) as a yellow solid (6.84 g)

NMR ($\delta_H$), ($CDCl_3$): 3.97 (3H, s), 6.90 (1H, m), 7.76 (1H, dd, J=5.9, 11.0 Hz), 10.34 (1H, s).

Description 19

5-Bromo-4-(methyloxy)-1H-indazole (D19)

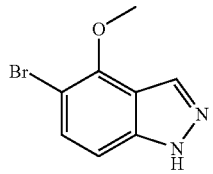

A mixture of 3-bromo-6-fluoro-2-(methyloxy)benzaldehyde (D18) (4 g, 17.16 mmol), methoxylamine hydrochloride (1.43 g, 17.16 mmol) and potassium carbonate (2.60 g, 18.97 mmol) in DME (20 mL) was stirred at room temperature for 5 hrs under argon. The mixture was filtered and the filtrate was concentrated then redissolved in DME (20 mL) and hydrazine hydrate (20 mL) was added and the mixture was heated to 100° C. for 16 hrs. After cooling, ethyl acetate was added and the organic layer was separated, washed with brine, dried (MgSO$_4$) and concentrated. Trituration with diethyl ether gave the title compound (D19) as an orange solid.

LC-MS: MH$^+$=227/229 (C$_8$H$_7$BrN$_2$O=226/228)

Description 20

5-Bromo-1-{3-fluoro-4-[(phenylmethyl)oxy]phenyl}-4-(methyloxy)-1H-indazole (D20)

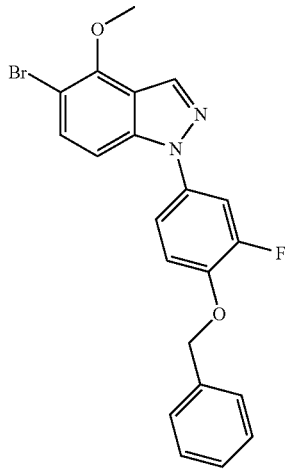

A mixture of 5-bromo-4-(methyloxy)-1H-indazole (D19) (0.670 g, 2.95 mmol), 4-benzyloxy-3-fluorobenzeneboronic acid (1.45 g, 5.90 mmol), copper (II) acetate (0.804 g, 4.43 mmol), pyridine (0.447 mL, 5.90 mmol) and powdered 4A molecular sieves (3 g) in dichloromethane (30 mL) was stirred in an air atmosphere at room temperature. After 4 days, the mixture was diluted with ethyl acetate and filtered through celite. The filtrate was washed with water, dried (Na$_2$SO$_4$) and concentrated. Chromatography on silica gel (0-30% ethyl acetate in hexane and diethyl ether in hexane) gave the title compound (D20) (0.65 g)

LC-MS: MH$^+$ at 427/429 (C$_{21}$H$_{16}$BrFN$_2$O$_2$=426/428)

Description 21

2-Bromo-3-chloro-6-fluorobenzaldehyde (D21)

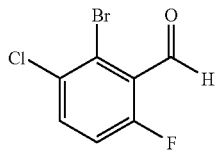

To a solution of diisopropylamine (5 mL, 35.4 mmol) in THF (30 mL) at 0° C. under argon was added n-butyl lithium (16.5 mL of 1.6 M solution in hexane, 26.4 mmol) slowly over 20 minutes. The mixture was cooled to −75° C. and 2-bromo-1-chloro-4-fluorobenzene (5 g, 23.9 mmol) in THF (20 mL) was added dropwise over 15 mins whilst maintaining the temperature <−70° C. The solution was then stirred at −75° C. for 45 mins and then DMF (2.2 mL, 28.6 mmol) was added over 5 mins. The mixture was stirred at −78° C. for 2 hrs and then allowed to reach room temperature. Water was added and the aqueous layer was extracted with ethyl acetate. The combined extracts were washed with brine and the solvent evaporated. Chromatography (silica gel, ethyl acetate/hexane) gave the title compound (D21) as a yellow solid (3.344 g)

NMR ($\delta_H$), (CDCl$_3$): 7.14 (1H, m), 7.66 (1H, dd, J=5.0, 11.0 Hz), 10.32 (1H, s)

Description 22

4-Bromo-5-chloro-1H-indazole (D22)

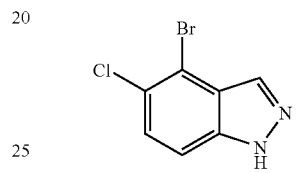

A mixture of 2-bromo-3-chloro-6-fluorobenzaldehyde (D21) (1 g, 4.2 mmol), methoxylamine hydrochloride (0.35 g, 4.2 mmol) and potassium carbonate (0.64 g, 4.6 mmol) was heated in anhydrous DME (5 mL) at 40° C. for 5 hrs. The mixture was filtered through celite and the filtrate concentrated to 1-2 mL. Hydrazine monohydrate (20 mL) was added and the mixture was heated at 100° C. for 21 hrs. After cooling, ethyl acetate and water were added and the aqueous layer was extracted with ethyl acetate. The combined extracts were washed with brine, dried and evaporated. Chromatography (silica, ethyl acetate/hexane) gave the title compound (D22) as an off white solid (0.361 g)

LC-MS: MH$^+$=231/233/235 (C$_7$H$_4$BrClN$_2$=230/232/234)

Description 23

4-Bromo-5-chloro-1-{3-fluoro-4-[(phenylmethyl)oxy]phenyl}-1H-indazole (D23)

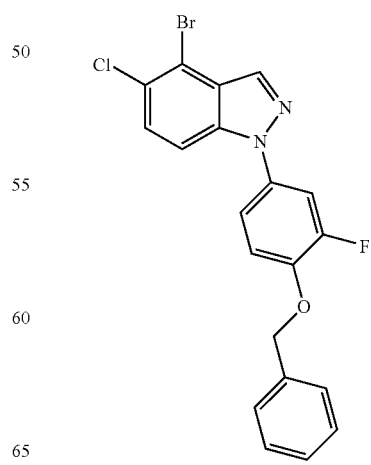

A mixture of 4-bromo-5-chloro-1H-indazole (D22) (0.361 g, 1.56 mmol), {3-fluoro-4-[(phenylmethyl)oxy] phenyl}boronic acid (0.57 g, 2.32 mmol), copper (II) acetate (0.42 g, 2.31 mmol) and pyridine (0.25 mL, 3.10 mmol) in dichloromethane (50 mL) were stirred together vigorously under an air atmosphere with powdered 4A molecular sieves (1.5 g). After 5 days, the mixture was filtered through celite and the solvent evaporated. The concentrate was chromatographed (silica, dichloromethane/hexane) to give the title compound (D23) as an off white solid (0.32 g)

LC-MS: MH$^+$=431/433 (C$_{20}$H$_{13}$BrClFN$_2$O=430/432)

Description 24

5-Chloro-1-{3-fluoro-4-[(phenylmethyl)oxy]phenyl}-1H-indazol-4-ol (D24)

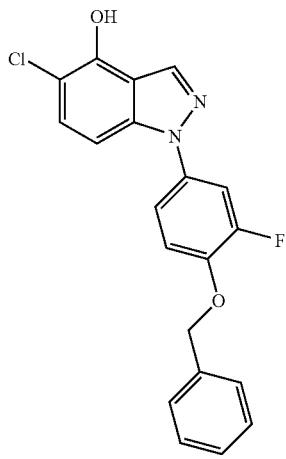

A suspension of 4-bromo-5-chloro-1-{3-fluoro-4-[(phenylmethyl)oxy]phenyl}-1H-indazole (D23) (0.32 g, 0.74 mmol) in 1,4-dioxane (5 mL)/water (5 mL) was stirred and treated with potassium hydroxide (0.17 g, 3.03 mmol), Pd$_2$dba$_3$ (0.014 g, 0.015 mmol) and 2-di-tertbutylphosphino-2',4',6'-triisopropylbiphenyl (0.019 g, 0.045 mmol) and the mixture was heated to 90° C. under argon. After 3 hrs, the mixture was cooled and water/ethyl acetate were added followed by 2N HCl (1.3 mL) and the product was extracted into ethyl acetate. The combined extracts were washed with brine, dried, concentrated and chromatographed (silica, ethyl acetate/hexane) to give the title compound (D24) (0.195 g)

LC-MS: MH$^+$=369/371 (C$_{20}$H$_{14}$ClFN$_2$O$_2$=368/370)

Description 25

2,3-Difluoro-6-(methyloxy)benzaldehyde (D25)

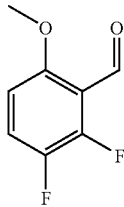

To a solution of diisopropylamine (14.6 mL, 103.5 mmol) in dry THF (50 mL) cooled to −78° C. was added a solution of BuLi (1.6 M in hexane, 47 mL, 75.9 mmol) dropwise under argon, keeping the temperature below −60° C. It was stirred at this temperature for 15 minutes after which a solution of 1,2-difluoro-4-(methyloxy)benzene (10 g, 69 mmol) in dry THF (50 mL) was added slowly. The mixture was left stirring at −78° C. for 45 minutes followed by slow addition of DMF (6.37 mL, 82.8 mmol) maintaining the temperature below −60° C. The resulting mixture was stirred at −78° C. for circa 3.5 hours after which water (100 mL) was added and the cooling removed to allow it to warm up to room temperature. It was diluted with EtOAc and the organic separated. The aqueous was re-extracted with EtOAc (3×) and the combined organics washed with brine and dried over MgSO$_4$. The crude material (10.26 g) was purified by flash chromatography to afford the title compound (D25) (9 g).

LC-MS: MH$^+$=173 (C$_8$H$_6$F$_2$O$_2$=172)

Description 26

7-Fluoro-4-(methyloxy)-1H-indazole (D26)

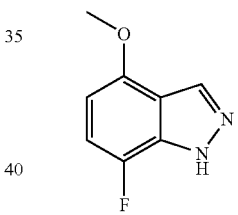

The 2,3-difluoro-6-(methyloxy)benzaldehyde (D25) (5 g, 29.05 mmol) was dissolved in DME (30 mL) and degassed by sonication under argon for 5 minutes. To this was added O-methylhydroxylamine hydrochloride (2.43 g, 29.05 mmol) and K$_2$CO$_3$ (4.42 g, 31.95 mmol) and the solution stirred for 3 hours. The mixture was filtered through celite and the volume reduced to approximately 20 mL under vacuo. To this was added hydrazine monohydrate (20 mL) and it was refluxed under argon for 2.5 days. The reaction was then cooled to room temperature, diluted with EtOAc (150 mL) and water (150 mL) and the phases separated. The aqueous layer was re-extracted with EtOAc (3×) and the combined organics were washed with brine and dried over MgSO$_4$. The crude material (4.8 g) was purified by flash chromatography (ISCO Companion XL, 120 g silica column) with a gradient of EtOAc (0 to 50%) in hexane to afford 3.33 g of title compound (D26).

LC-MS: MH$^+$=167 (C$_8$H$_7$FN$_2$O=166)

Description 27

7-Fluoro-1-{3-fluoro-4-[(phenylmethyl)oxy]phenyl}-4-(methyloxy)-1H-indazole (D27)

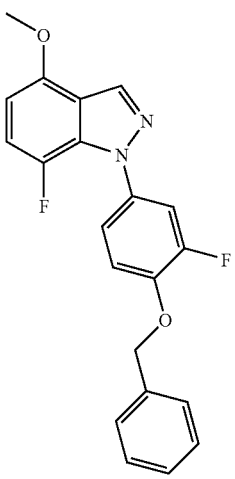

7-Fluoro-4-(methyloxy)-1H-indazole (D26) (500 mg, 3.01 mmol), the {3-fluoro-4-[(phenylmethyl)oxy]phenyl}boronic acid (1.48 g, 6.02 mmol), copper (II) acetate (820 mg, 4.51 mmol), powdered molecular sieves (550 mg) and pyridine (0.49 mL, 6.02 mmol) in DCM (15 mL) were stirred at room temperature in the presence of air. After 4 hours the mixture was filtered through a pad of celite and washed with water. The aqueous was re-extracted with DCM (3×) and the combined organics were washed with brine and dried over $MgSO_4$. The crude (1.71 g) was purified by flash chromatography (Biotage SP4) with a gradient of EtOAc (0 to 20%) in hexane to afford 286 mg of title compound (D27).

LC-MS: $MH^+$=367 ($C_{21}H_{18}F_2N_2O_2$=366)

Description 28

7-Chloro-4-(methyloxy)-1H-indazole (D28)

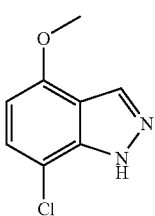

To a solution of 3-chloro-2-fluoro-6-(methyloxy)benzaldehyde (10 g, 53.0 mmol) in 1,2-dimethoxyethane (105 mL) was added potassium carbonate (8.06 g, 58.3 mmol) and O-methylhydroxylamine hydrochloride (4.43 g, 53.0 mmol) and the mixture was stirred and heated at 45° C. for 4 hrs. After cooling, the mixture was filtered and concentrated to ~40 mL and hydrazine monohydrate (58.3 mL, 1856 mmol) was added and the reaction was refluxed under argon over the weekend. The mixture was concentrated to 10-15 mL on the rotary evaporator and then poured into water and stirred for 10 mins. The precipitated solid was collected by filtration and washed with water (3×), sucked dry and then dried in the vacuum oven at 60° C. for 1 hr to give the title compound (D28) as an off white solid (8.83 g)

LC-MS: $MH^+$=183/185 ($C_8H_7ClN_2O$=182/184)

Description 29

7-Chloro-1-{3-fluoro-4-[(phenylmethyl)oxy]phenyl}-4-(methyloxy)-1H-indazole (D29)

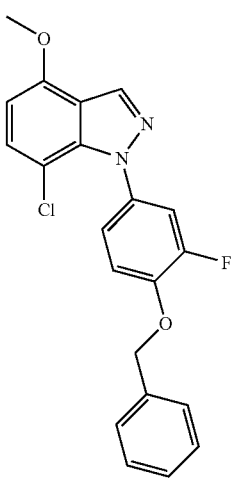

A mixture of 7-chloro-4-(methyloxy)-1H-indazole (D28) (5 g, 27.4 mmol), {3-fluoro-4-[(phenylmethyl)oxy]phenyl}boronic acid (10.11 g, 41.1 mmol), copper (II) acetate (7.46 g, 41.1 mmol) and pyridine (4.43 mL, 4.33 g, 54.8 mmol) in dichloromethane (100 mL) were stirred together vigorously under an air atmosphere with powdered 4A molecular sieves (~25 g). After 4 days, the mixture was filtered through celite and the filter washed with dichloromethane. The filtrate was washed with water and brine and then dried ($Na_2SO_4$) and evaporated. Chromatography (silica, 5-100% dichloromethane in isohexane) gave 2 products, the more polar component was the N-1 arylated product (off white solid 2.41 g) (D29).

LC-MS: $MH^+$=383/385 ($C_{21}H_{16}ClFN_2O_2$=382/384)

Description 30

3-Methyl-4-[(phenylmethyl)oxy]-1H-indazole (D30)

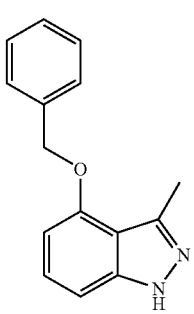

To a suspension of sodium hydride (0.452 g of a 60% dispersion in mineral oil, 11.3 mmol) in DMF (30 mL) was added 4-hydroxy-3-methylindazole (1.52 g, 10.3 mmol) (prepared in a similar manner to that described in J. Med Chem., 2000, 2672) in DMF (20 mL) via a cannula. The mixture was stirred at room temperature for 10 minutes and then benzyl bromide (1.223 mL, 10.3 mmol) was added and stirring was continued at room temperature for 2 hrs. The mixture was quenched with ammonium chloride solution and the DMF was evaporated. Ethyl acetate and water were added and the product was extracted into ethyl acetate and the extracts were dried ($Na_2SO_4$) and evaporated. Chromatography (0-100% ethyl acetate in hexane) gave the title compound (D30) as an orange solid (1.774 g, containing ~10% dibenzylated material).

LC-MS: $MH^+$=239 ($C_{15}H_{14}N_2O$=238)

Description 31

1-{3-Fluoro-4-[(phenylmethyl)oxy]phenyl}-3-methyl-4-[(phenyl methyl)oxy]-1H-indazole (D31)

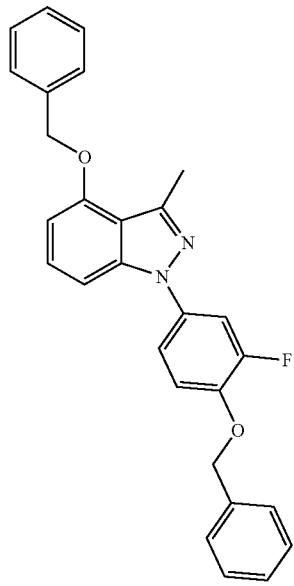

A mixture of 3-methyl-4-[(phenylmethyl)oxy]-1H-indazole (D30) (0.952 g, 4 mmol), 4-benzyloxy-3-fluorobenzeneboronic acid (1.97 g, 8.0 mmol), copper (II) acetate (1.09 g, 6.0 mmol), pyridine (0.647 mL, 8.0 mmol) and powdered 4A molecular sieves (4 g) in dichloromethane (25 mL) was stirred in an air atmosphere at room temperature. After 48 hrs, the mixture was filtered through Celite, concentrated, redissolved in ethyl acetate, refiltered and concentrated and then chromatographed (0-50% ethyl acetate in hexane and 0-40% diethyl ether in hexane). A white solid crystallised out from some fractions and this was collected by filtration to give the title compound (D31) (0.45 g).

LC-MS: $MH^+$=439 ($C_{28}H_{23}FN_2O_2$=438)

Description 32

1-[4-(Methyloxy)phenyl]-4-[(phenylmethyl)oxy]-1H-indazole (D32)

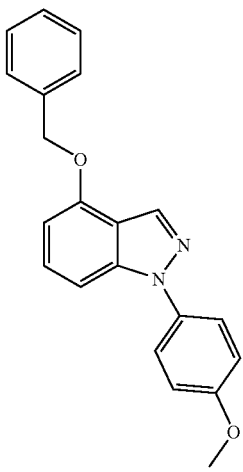

The 4-[(phenylmethyl)oxy]-1H-indazole (D1) (543 mg, 1.65 mmol), the [4-(methyloxy)phenyl]boronic acid (500 mg, 3.29 mmol), copper (II) acetate (448 mg, 2.47 mmol), powdered molecular sieves (400 mg) and pyridine (0.27 mL, 3.29 mmol) in DCM (75 mL) were stirred at room temperature in the presence of air. After 4 hours the mixture was filtered through a pad of celite and washed with water. The aqueous was re-extracted with DCM and the combined organics were washed with brine and dried over $MgSO_4$. The crude (880 mg) was purified by flash chromatography (Biotage SP4) with a gradient of $Et_2O$ (0 to 30%) in hexane to afford 115 mg of title compound (D32).

LC-MS: $MH^+$=331 ($C_{21}H_{18}N_2O_2$=330)

Description 33

1-[3-Chloro-4-(methyloxy)phenyl]-4-[(phenylmethyl)oxy]-1H-indazole (D33)

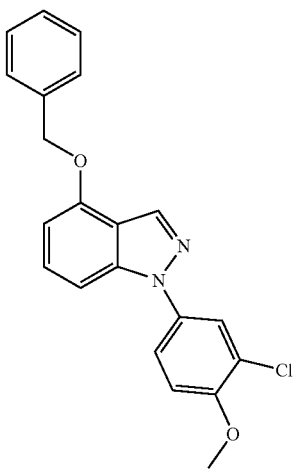

The 4-[(phenylmethyl)oxy]-1H-indazole (D1) (500 mg, 2.23 mmol), the [3-chloro-4-(methyloxy)phenyl]boronic acid (831 mg, 4.46 mmol), copper (II) acetate (608 mg, 3.345 mmol), powdered molecular sieves (400 mg) and pyridine (0.36 mL, 4.46 mmol) in DCM (75 mL) were stirred at room temperature in the presence of air. After 5 days the mixture was filtered through a pad of celite and washed with water. The aqueous was re-extracted with DCM and the combined organics were washed with brine and dried over MgSO$_4$. The crude (1.06 g) was purified by flash chromatography (Biotage SP4, 40+M silica column) with a gradient of EtOAc (0 to 20%) in hexane to afford 470 mg of title compound (D33) containing an impurity.

LC-MS: MH$^+$=365 (C$_{21}$H$_{17}$ClN$_2$O$_2$=364)

Description 34

1-[3-Methyl-4-(methyloxy)phenyl]-4-[(phenylmethyl)oxy]-1H-indazole (D34)

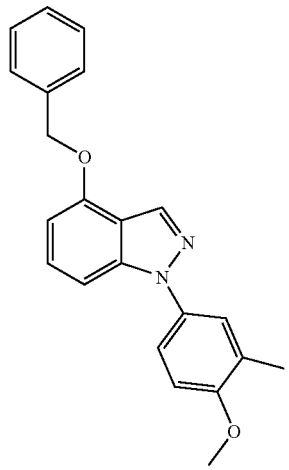

The 4-[(phenylmethyl)oxy]-1H-indazole (D1) (500 mg, 2.23 mmol), the [3-methyl-4-(methyloxy)phenyl]boronic acid (740 mg, 4.46 mmol), copper (II) acetate (608 mg, 3.345 mmol), pyridine (0.36 mL, 4.46 mmol) and powdered molecular sieves (400 mg) in DCM (75 mL) were stirred at room temperature in the presence of air. After 41 hours the mixture was filtered through a pad of celite and washed with water. The aqueous was re-extracted with DCM and the combined organics were washed with brine and dried over MgSO$_4$. The crude (1.17 g) was purified by flash chromatography (Biotage SP4) with a gradient of EtOAc 0 to 30% in hexane to afford 562 mg of title compound (D34) containing an impurity.

LC-MS: MH$^+$=345 (C$_{22}$H$_{20}$N$_2$O$_2$=344)

Description 35

1-{3,5-Difluoro-4-[(phenyl methyl)oxy]phenyl}-4-[(phenylmethyl)oxy]-1H-indazole (D35)

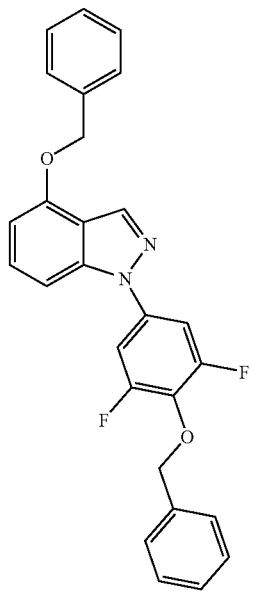

To a solution of 4-[(phenylmethyl)oxy]-1H-indazole (D1) (280 mg, 1.25 mmol) in dichloromethane (20 mL) was added {3,5-difluoro-4-[(phenylmethyl)oxy]phenyl}boronic acid {DE patent application 4236105} (660 mg, 2.50 mmol), pyridine (0.202 mL, 2.50 mmol), copper acetate (340 mg, 1.88 mmol) and powdered 4A molecular sieves (500 mg). The reaction mixture was stirred at room temperature in the presence of air for 6 days. Celite was added to the mixture then the mixture was filtered through a pad of celite and then the filtrate was washed with water. After separation of the layers, the aqueous phase was re-extracted with dichloromethane. The combined organic layers were dried over magnesium sulphate, filtered and concentrated. The product was purified by silica gel chromatography eluting with 5-100% ethyl acetate in hexane to yield the title compound (D35 (257 mg).

LC-MS: MH$^+$=443 (C$_{27}$H$_{20}$F$_2$N$_2$O$_2$=442)

Description 36

4-Bromo-1-{3,5-difluoro-4-[(phenylmethyl)oxy]phenyl}-1H-indazole-6-carbonitrile (D36)

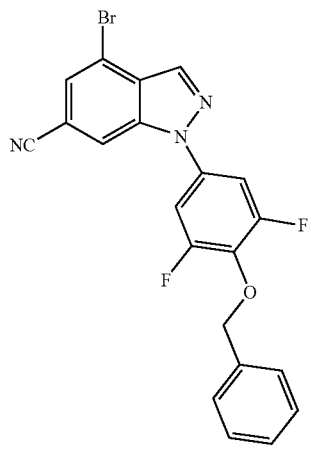

To a solution of 4-bromo-1H-indazole-6-carbonitrile (1.0 g, 4.50 mmol) in dichloromethane (50 mL) was added {3,5-difluoro-4-[(phenylmethyl)oxy]phenyl}boronic acid {DE 4236105} (1.8 g, 6.82 mmol), pyridine (0.73 mL, 9.04 mmol), copper acetate (1.22 g, 6.74 mmol) and powdered 4A molecular sieves (5 g). The reaction mixture was stirred at room temperature in the presence of air for 6 days. Celite was added to the mixture and stirred for 5 mins then the mixture was filtered through a pad of celite and then the filtrate was washed with water, dried over magnesium sulphate, filtered and concentrated. The product was purified by silica gel chromatography eluting with 10-100% ethyl acetate in hexane to yield the title compound (D36) (944 mg).

LC-MS: MH$^+$=440, 442 (C$_{21}$H$_{12}$BrF$_2$N$_3$O=439, 441)

Description 37

1-{3,5-Difluoro-4-[(phenylmethyl)oxy]phenyl}-4-hydroxy-1H-indazole-6-carbonitrile (D37)

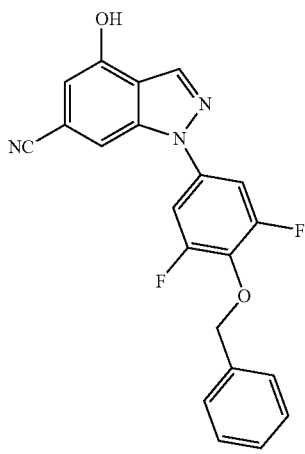

To a solution of 4-bromo-1-{3,5-difluoro-4-[(phenylmethyl)oxy]phenyl}-1H-indazole-6-carbonitrile (D36) (940 mg, 2.135 mmol) in dioxane (20 mL) and water (20 mL) was added potassium hydroxide (479 mg, 8.54 mmol). The mixture was degassed with argon and then treated with 2-di-tert-butylphosphino-2',4',6'-triisopropylbiphenyl (54.4 mg, 0.128 mmol) and tris(dibenzylideneacetone)dipalladium(0) (39.1 mg, 0.043 mmol). The reaction mixture was heated to 90° C. for 1 hour. The reaction was diluted with ethyl acetate and water. After separation of the layers, the aqueous phase was re-extracted with ethyl acetate. The combined organic layers were dried over magnesium sulphate, filtered and concentrated in vacuo. The product was purified by silica gel chromatography eluting with 10-100% ethyl acetate in hexane to give the title compound (D37) (617 mg).

LC-MS: MH$^+$=378 (C$_{21}$H$_{13}$F$_2$N$_3$O$_2$=377)

Description 38

4-Bromo-1-{3-fluoro-4-[(phenylmethyl)oxy]phenyl}-1H-indazole (D38)

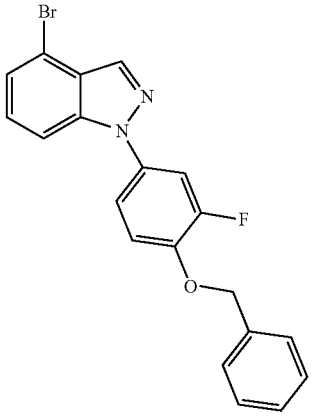

To a solution of 4-bromo-1H-indazole (4.32 g, 21.9 mmol) in dichloromethane (100 mL) was added 4-benzyloxy-3-fluorobenzeneboronic acid (10.8 g, 43.9 mmol), pyridine (3.5 mL, 43.3 mmol), copper acetate (5.9 g, 32.6 mmol) and powdered 4A molecular sieves (5 g). The reaction mixture was stirred at room temperature in the presence of air for 5 days. Celite was added to the reaction mixture and the mixture stirred for 5 minutes. The mixture was then filtered through a pad of celite and washed with dichloromethane and then the filtrate concentrated in vacuo. The residue was diluted in dichloromethane and water. After separation of the layers, the aqueous phase was extracted with dichloromethane (×4). The combined organic layers were dried over magnesium sulphate, filtered and concentrated in vacuo. The product was purified by silica gel chromatography eluting with 10-80% dichloromethane in hexane to yield the title compound (D38) (5.25 g).

LC-MS: MH$^+$=397, 399 (C$_{20}$H$_{14}$BrFN$_2$O=396, 398)

$^1$H NMR $\delta_H$ (d$_s$-DMSO) 8.34 (1H, d, J 0.9 Hz), 7.80 (1H, m), 7.69 (1H, dd, J 12.0, 2.5 Hz), 7.56-7.35 (9H, m), 5.29 (2H, s).

Description 39

1-{3-Fluoro-4-[(phenylmethyl)oxy]phenyl}-1H-indazol-4-ol (D39)

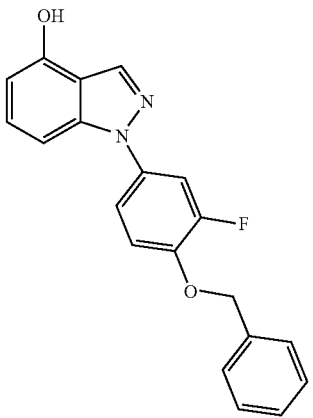

To a solution of 4-bromo-1-{3-fluoro-4-[(phenylmethyl)oxy]phenyl}-1H-indazole (D38) (5.25 g, 13.2 mmol) in dioxane (50 mL) and water (50 mL) was added potassium hydroxide (2.95 g, 52.7 mmol). The reaction mixture was degassed with argon and then treated with bis(1,1-dimethylethyl)[2',4',6'-tris(1-methylethyl)-2-biphenylyl]phosphane (336 mg, 0.79 mmol) and tris(dibenzylideneacetone)dipalladium (0) (242 mg, 0.26 mmol). After heating at 90° C. for 1 hour under argon, the mixture was allowed to cool to room temperature and then diluted with ethyl acetate and water. The pH was adjusted to ~7 by the addition of 1M hydrochloric acid. After separation of the layers, the aqueous phase was re-extracted with ethyl acetate. The combined organic layers were dried over magnesium sulphate, filtered and concentrated in vacuo. The product was purified by silica gel chromatography eluting with 5-70% ethyl acetate in hexane to yield the title compound (D39) (3.80 g).

LC-MS: MH$^+$=335 ($C_{20}H_{15}FN_2O_2$=334)

$^1$H NMR $\delta_H$ (d$_6$-DMSO) 10.41 (1H, s), 8.31 (1H, d, J 0.9 Hz), 7.61 (1H, dd, J 12.2, 2.5 Hz), 7.52-7.17 (9H, m), 6.55 (1H, d J 7.5 Hz), 5.26 (2H, s).

Example 1

1-(3-Fluoro-4-hydroxyphenyl)-1H-indazol-4-ol (E1)

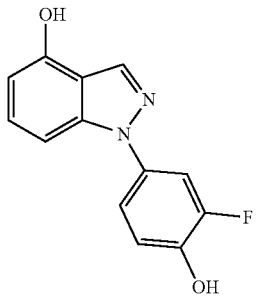

A mixture of 1-{3-fluoro-4-[(phenylmethyl)oxy]phenyl}-4-[(phenylmethyl)oxy]-1H-indazole (D2) (307 mg) in ethanol/ethyl acetate (~50 mL, 1:1) was hydrogenated in the presence of 10% Pd on charcoal (150 mg) at atmospheric pressure and room temperature for 3 hrs. The mixture was filtered and concentrated and then chromatographed on silica gel (elution with 0-50% ethyl acetate in hexane) to give an off white solid. This was dissolved in ethyl acetate and stirred with charcoal (Norit SX+, 10 mg) for 30 minutes. The mixture was filtered and concentrated to give the title compound (E1) (144 mg).

LC-MS: MH$^+$=245 ($C_{13}H_9FN_2O_2$=243)

NMR ($\delta_H$), (d$_6$-DMSO): 6.54 (1H, d, J=7.5 Hz), 7.13 (1H, t, J=7.9 Hz), 7.14 (1H, d, J=8.4 Hz), 7.25 (1H, dd, J=7.8, 8.4 Hz), 7.36 (1H, ddd, J=1.3, 2.6, 8.7 Hz), 7.49 (1H, dd, J=2.7, 12.0 Hz), 8.27 (1H, d, J=0.6 Hz), 10.17 (1H, broad s), 10.29 (1H, broad s) ppm Example 1a 1-(3-Fluoro-4-hydroxyphenyl)-1H-indazol-4-ol (E1), alternative procedure A solution of 1-{3-fluoro-4-[(phenylmethyl)oxy]phenyl}-1H-indazol-4-ol (D39) (3.79 g, 11.3 mmol) in ethyl acetate (150 mL) was hydrogenated overnight at room temperature and pressure over 10% palladium on charcoal (700 mg). The mixture was filtered through a pad of celite, washed with ethyl acetate and the resulting filtrate was concentrated in vacuo. The product was purified by silica gel chromatography eluting with 5-80% ethyl acetate in hexane. The product was then triturated with hexane and the product collected by filtration and dried in a vacuum oven to yield the title compound (E1a) (2.35 g).

LC-MS and NMR data were consistent with those described for Example 1

Example 2

1-(3-Fluoro-4-hydroxyphenyl)-6-(methyloxy)-1H-indazol-4-ol (E2)

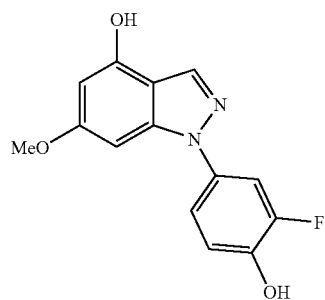

A solution of 1-{3-fluoro-4-[(phenylmethyl)oxy]phenyl}-6-(methyloxy)-1H-indazol-4-ol (D4) (116 mg, 0.32 mmol) in ethanol (5 mL) and ethyl acetate (5 mL) was hydrogenated in an H-cube over a 10% palladium on charcoal catalyst. The resulting solution was concentrated and the product purified by silica gel chromatography eluting with 5-80% ethyl acetate in hexane to yield the title compound (E2) (65 mg).

LC-MS: MH$^+$=275 ($C_{14}H_{11}FN_2O_3$=274)

Example 3

1-(3-Fluoro-4-hydroxyphenyl)-4-hydroxy-1H-indazole-6-carbonitrile (E3)

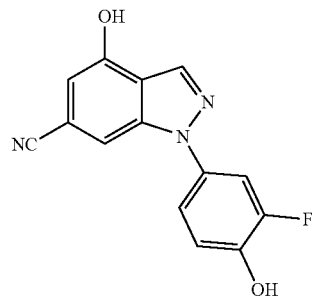

A solution of 1-{3-fluoro-4-[(phenylmethyl)oxy]phenyl}-4-hydroxy-1H-indazole-6-carbonitrile (D6) (308 mg, 0.86 mmol) in ethanol (10 mL) and ethyl acetate (10 mL) was hydrogenated in an H-cube over a 10% palladium on charcoal catalyst. The resulting solution was concentrated, dissolved in ethanol then the product purified by silica gel chromatography eluting with 10-100% ethyl acetate in hexane to yield the title compound (E3) (98 mg).

LC-MS: MH$^+$=270 ($C_{14}H_8FN_3O_2$=269)

$^1$H NMR $\delta_H$ (d6-DMSO) 11.23 (1H, s), 10.32 (1H, s), 8.44 (1H, d, J 0.9 Hz), 7.71 (1H, m), 7.57 (1H, dd, J 11.8, 2.6 Hz), 7.39 (1H, m), 7.14 (1H, dd, J 9.4, 8.8 Hz), 6.77 (1H, d, J 1.1 Hz).

Example 4

6-Fluoro-1-(3-fluoro-4-hydroxyphenyl)-1H-indazol-4-ol (E4)

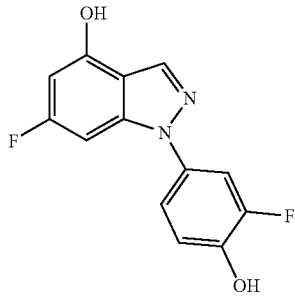

A solution of 6-fluoro-1-{3-fluoro-4-[(phenylmethyl)oxy]phenyl}-1H-indazol-4-ol (D8) (470 mg, 1.34 mmol) in ethanol (20 mL) and ethyl acetate (20 mL) was hydrogenated in an H-cube over a 10% palladium on charcoal catalyst. The resulting solution was concentrated to yield the title compound (E4) (320 mg).

LC-MS: MH$^+$=263 ($C_{13}H_8F_2N_2O_2$=262)

$^1$H NMR $\delta_H$ (d6-DMSO) 10.96 (1H, s), 10.19 (1H, s), 8.27 (1H, d, J 0.9 Hz), 7.49 (1H, dd, J 11.8, 2.6 Hz), 7.34 (1H, m), 7.12 (1H, dd, J 9.5, 8.7 Hz), 6.92 (1H, m), 6.38 (1H, dd, J 11.2, 2.0 Hz).

Example 5

6-Bromo-1-(3-fluoro-4-hydroxyphenyl)-1H-indazol-4-ol (E5)

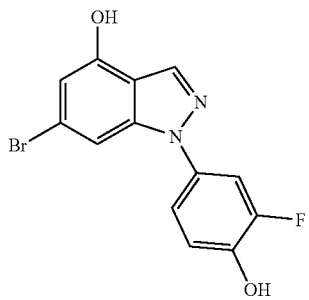

48% Hydrobromic acid (10 mL) was added to 6-bromo-1-{3-fluoro-4-[(phenylmethyl)oxy]phenyl}-4-(methyloxy)-1H-indazole (D9) (1.16 g, 2.71 mmol) and the mixture heated at 130° C. for 3 hours. After cooling to room temperature, the mixture was diluted with ethyl acetate and water. The pH was adjusted to 7 by the addition of 2M aqueous sodium hydroxide solution. After separation of the organic layer, the aqueous phase was re-extracted with ethyl acetate. The combined organic layers were dried over magnesium sulphate, filtered and concentrated. The crude product was purified by silica gel chromatography eluting with 5-100% ethyl acetate in hexane. The product was further purified by MDAP to yield the title compound (E5) (170 mg).

LC-MS: MH$^+$=323/325 ($C_{13}H_8BrFN_2O_2$=322/324)

Example 6

6-Ethenyl-1-(3-fluoro-4-hydroxyphenyl)-1H-indazol-4-ol (E6)

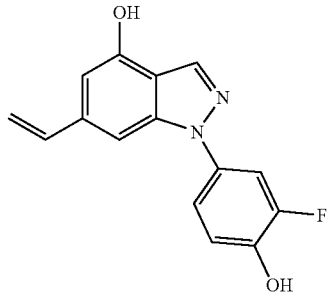

To a solution of 6-bromo-1-(3-fluoro-4-hydroxyphenyl)-1H-indazol-4-ol (360 mg, 1.11 mmol) (E5) in dimethoxyethane (10 mL) was added dichlorobis(tris-o-tolylphosphine)palladium (44 mg, 0.056 mmol) and tributylvinyltin (0.65 mL, 2.22 mmol). The reaction mixture was heated at 90° C. under argon overnight. After cooling to room temperature, the mixture was filtered through a pad of celite. The filtrate was concentrated and the crude product purified by silica gel chromatography eluting with 5-100% ethyl acetate in hexane. The product was further purified by MDAP to yield the title compound (E6) (101 mg).

LC-MS: MH$^+$=271 ($C_{15}H_{11}FN_2O_2$=270)

Example 7

6-Ethyl-1-(3-fluoro-4-hydroxyphenyl)-1H-indazol-4-ol (E7)

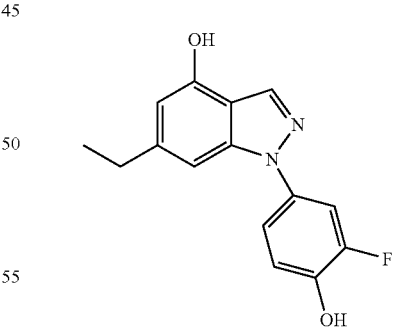

A solution of 6-ethenyl-1-(3-fluoro-4-hydroxyphenyl)-1H-indazol-4-ol (E6) (190 mg, 0.70 mmol) in ethanol (6 mL) and ethyl acetate (6 mL) was hydrogenated over a weekend at room temperature and a pressure of 50 psi over a 10% palladium on charcoal catalyst (20 mg). After filtration to remove the catalyst, the filtrate was concentrated and the crude product purified using MDAP to yield the title compound (E7) (36 mg).

LC-MS: MH$^+$=273 ($C_{15}H_{13}FN_2O_2$=272)

Example 8

6-Chloro-1-(3-fluoro-4-hydroxyphenyl)-1H-indazol-4-ol (E8)

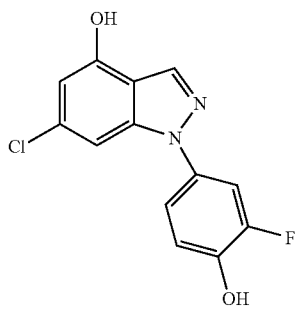

To a suspension of 6-chloro-1-{3-fluoro-4-[(phenylmethyl)oxy]phenyl}-1H-indazol-4-ol (D11) (60 mg, 0.163 mmol) in dry DCM (2 mL) cooled to −78° C. was added BBr$_3$ (1M in DCM, 0.326 mL, 0.326 mmol) dropwise. The resulting mixture was stirred at this temperature for 1 hour, then it was warmed to room temperature, treated with water and the pH adjusted to 7 by addition of saturated NaHCO$_3$. The solution was extracted with EtOAc (2×) and the combined organics were dried over MgSO$_4$. The crude material (49 mg) was then purified by flash chromatography with a gradient of 5-100% EtOAc in hexane to give a the title compound (E8) as a colourless solid (35 mg).

LC-MS: MH$^+$=279 (C$_{13}$H$_8$ClFN$_2$O$_2$=278)

NMR (δ$_H$), (d$_6$-DMSO): 6.54 (1H, d, J=1.6 Hz), 7.16 (2H, m), 7.34 (1H, ddd, J=1.2, 2.8, 8.8 Hz), 7.50 (1H, dd, J=2.8, 12 Hz), 8.29 (1H, s), 10.25 (1H, bs), 10.95 (1H, bs).

Example 9

1-(3-Fluoro-4-hydroxyphenyl)-6-methyl-1H-indazol-4-ol (E9)

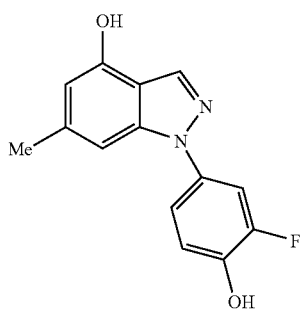

The title compound was prepared via a procedure similar to that described in Example 8 starting from 1-{3-fluoro-4-[(phenylmethyl)oxy]phenyl}-6-methyl-1H-indazol-4-ol (D13) (720 mg, 2.01 mmol). The final purification yielded 142 mg of title compound as a yellow solid.

LC-MS: MH$^+$=259 (C$_{14}$H$_{11}$FN$_2$O$_2$=258)

NMR (δ$_H$), (d$_6$-DMSO): 2.35 (3H, s), 6.37 (1H, s), 6.94 (1H, s), 7.12 (1H, t, J=8.8 Hz), 7.33 (1H, ddd, J=1.2, 2.4, 8.8 Hz), 7.46 (1H, dd, J=2.8, 12 Hz), 8.18 (1H, s), 10.2 (2H, bs).

Example 10

5-Fluoro-1-(3-fluoro-4-hydroxyphenyl)-1H-indazol-4-ol (E10)

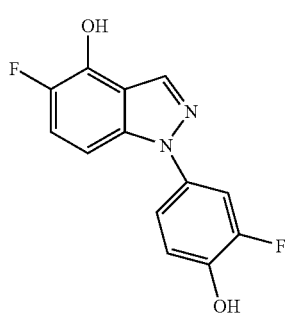

A solution of 5-fluoro-1-{3-fluoro-4-[(phenylmethyl)oxy]phenyl}-1H-indazol-4-ol (D17) (610 mg, 1.731 mmol) in ethanol (20 mL) was hydrogenated with 10% palladium on carbon (0.25 g, 2.349 mmol) at room temperature for 2 hrs. The mixture was filtered, concentrated and chromatographed (0-100% EtOAc in hexane) to give the title compound (E10) as an off white solid (290 mg)

LC-MS: MH$^+$=263 (C$_{13}$H$_8$F$_2$N$_2$O$_2$=262)

NMR (δ$_H$), (d$_6$-DMSO) 7.12 (2H, m), 7.33 (2H, m), 7.50 (1H, dd, J=2.4, 12.0 Hz), 8.57 (1H, s), 10.23 (1H, broad s), 10.66 (1H, broad s).

Example 11

5-Bromo-1-(3-fluoro-4-hydroxyphenyl)-1H-indazol-4-ol (E11)

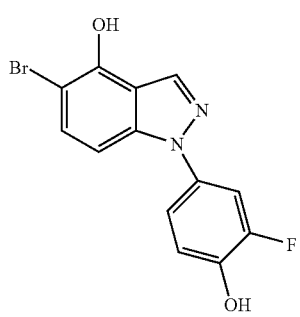

A solution of 5-bromo-1-{3-fluoro-4-[(phenylmethyl)oxy]phenyl}-4-(methyloxy)-1H-indazole (D20) (71 mg) in dry dichloromethane (2 mL) was cooled to −78° C. under argon and treated dropwise with boron tribromide solution (0.75 mL of 1M solution in dichloromethane, 0.75 mmol). The mixture was allowed to reach room temperature and was stirred overnight. Water and ethyl acetate were added and the pH of the aqueous layer was adjusted to 7 and the product was extracted into ethyl acetate. The extracts were dried (Na$_2$SO$_4$), concentrated and chromatographed (silica gel, 0-100% ethyl acetate in hexane) to give the title compound (E11) as a beige solid (40 mg)

LC-MS: MH$^+$=323/325 (C$_{13}$H$_8$N$_2$O$_2$BrF=322/324)

NMR ($\delta_H$), (d$_6$-DMSO): 7.13 (2H, m), 7.33 (1H, m), 7.49 (2H, m), 8.45 (1H, s), 10.22 (1H, s), 11.00 (1H, s)

Example 12

5-Chloro-1-(3-fluoro-4-hydroxyphenyl)-1H-indazol-4-ol (E12)

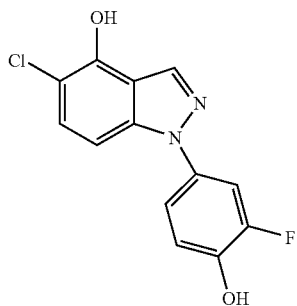

A solution of 5-chloro-1-{3-fluoro-4-[(phenylmethyl)oxy]phenyl}-1H-indazol-4-ol (D24) (0.072 g, 0.2 mmol) in dichloromethane (4 mL) was cooled to −78° C. and boron tribromide (0.4 mL of 1M solution in dichloromethane, 0.4 mmol) was added dropwise over 5 mins. After stirring at −78° C. for 3 hrs under argon, methanol (1 mL) was added and the mixture was diluted with dichloromethane (30 mL) and water (30 mL). The pH was adjusted to 7 with NaHCO$_3$ solution and the aqueous layer was separated and extracted with ethyl acetate (35 mL×2). The combined extracts were washed with brine (25 mL), and evaporated. The product was purified by MDAP to give the title compound (E12) as a white solid (0.022 g).

LC-MS: MH$^+$=279/281 (C$_{13}$H$_8$ClFN$_2$O$_2$=278/280)

NMR ($\delta_H$), (d$_6$-DMSO): 7.15 (2H, m), 7.36 (2H, m), 7.50 (1H, dd, J=2.4, 12.1 Hz), 8.43 (1H, s), 10.24 (1H, s), 11.01 (1H, s)

Example 13

7-Fluoro-1-(3-fluoro-4-hydroxyphenyl)-1H-indazol-4-ol (E13)

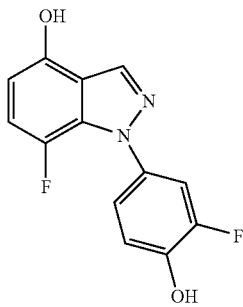

7-Fluoro-1-{3-fluoro-4-[(phenylmethyl)oxy]phenyl}-4-(methyloxy)-1H-indazole (D27) (280 mg, 0.764 mmol) was dissolved in HBr (48% aq., 15 mL) and refluxed at 120° C. under argon. After 2 hours the mixture was partitioned between DCM (50 mL)/water (50 mL), the pH adjusted to 7 by addition of a 2M solution of NaOH and the layers separated. The aqueous phase was extracted with DCM (3×50 mL) and the combined organics were washed with brine (50 mL), separated and dried over MgSO$_4$, filtered and concentrated in vacuo. The crude material (198 mg) was purified by flash chromatography (Biotage SP4) with a gradient of 0-100% Et$_2$O in hexane. The isolated material (75 mg) was further purified by MDAP to afford 46 mg of the title compound (E13).

LC-MS: MH$^+$=263 (C$_{13}$H$_8$F$_2$N$_2$O$_2$=262)

NMR ($\delta_H$), (d$_6$-DMSO): 6.40 (1H, dd, J=2.8, 8.4 Hz), 7.07 (2H, m), 7.24 (1H, d, J=8.8 Hz), 7.42 (1H, dd, J=2.8, 9.2 Hz), 8.3 (1H, s), 10.3 (2H, bs).

Example 14

7-Chloro-1-(3-fluoro-4-hydroxyphenyl)-1H-indazol-4-ol (E14)

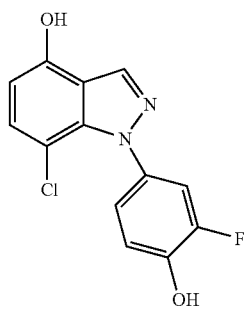

A mixture of 7-chloro-1-{3-fluoro-4-[(phenylmethyl)oxy]phenyl}-4-(methyloxy)-1H-indazole (D29) (2.41 g, 6.30 mmol) in 48% hydrobromic acid (120 mL) was heated to reflux and reaction was followed by LC-MS. After 2 hrs, the mixture was concentrated to ~30 mL on the rotary evaporator and then solid NaHCO$_3$ was added to pH 6. The product was extracted into ethyl acetate and the extracts were dried (Na$_2$SO$_4$) and concentrated. This product was dissolved in dichloromethane (60 mL) and cooled to −78° C. under argon and boron tribromide (2.381 mL, 25.2 mmol) was added dropwise via syringe. After 10 mins at −78° C., the mixture was allowed to reach room temperature and stirring was continued for 24 hrs. The mixture was diluted with ethyl acetate and NaHCO$_3$/water and the pH adjusted to 6 and the product was extracted into ethyl acetate. The extracts were dried (Na$_2$SO$_4$), concentrated and chromatographed (silica, 10% methanol in dichloromethane to crude product that was recolumned by 0-100% ethyl acetate in hexane) to give the title compound as an off-white powder (405 mg) (E14).

LC-MS: MH$^+$=279/281 (C$_{13}$H$_8$ClFN$_2$O$_2$=278/280)

NMR ($\delta_H$), (d$_6$-DMSO): 6.51 (1H, d, J=8.4 Hz), 7.04 (1H, m), 7.14 (1H, m), 7.24 (1H, d, J=8.4 Hz), 7.36 (1H, dd, J=2.4, 11.6 Hz), 8.30 (1H, s), 10.33 (1H, broad s), 10.59 (1H, broad s).

Example 15

1-(3-Fluoro-4-hydroxyphenyl)-3-methyl-1H-indazol-4-ol (E15)

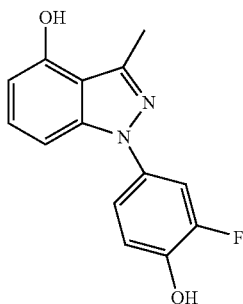

A mixture of 1-{3-fluoro-4-[(phenylmethyl)oxy]phenyl}-3-methyl-4-[(phenylmethyl)oxy]-1H-indazole (D31) (0.45 g) and 10% palladium on charcoal (150 mg) in ethyl acetate (30 mL) was hydrogenated at atmospheric pressure for about 18 hrs. The mixture was filtered, concentrated and chromatographed (silica gel, 0-100% ethyl acetate in hexane) to give the title compound as a white solid (0.15 g) (E15).

LC-MS: MH$^+$=259 (C$_{14}$H$_{11}$N$_2$O$_2$F=258)

NMR ($\delta_H$), (d$_6$-DMSO): 2.62 (3H, s), 6.48 (1H, d, J=7.2 Hz), 7.07 (2H, m), 7.18 (1H, m), 7.31 (1H, m), 7.43 (1H, dd, J=2.8, 8.0 Hz), 10.15 (2H, broad s)

Example 16

1-(4-Hydroxyphenyl)-1H-indazol-4-ol (E16)

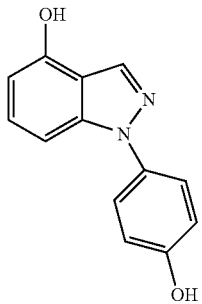

1-[4-(Methyloxy)phenyl]-4-[(phenylmethyl)oxy]-1H-indazole (D32) (40 mg, 0.121 mmol) was dissolved in dry DCM (1.5 mL) under argon and cooled to −78° C. in a dry ice-acetone bath. After 5 minutes BBr$_3$ (1M in DCM, 0.242 mL, 0.242 mmol) was added dropwise and when the addition was complete the bath was removed and it was allowed to reach room temperature. The reaction was followed by LC-MS. After 4 hours more BBr$_3$ (1M in DCM, 0.242 mL, 0.242 mmol) was added to the mixture and after 21 hours it was concentrated in vacuo. The residue was partitioned between EtOAc (25 mL)/water (25 mL), the pH adjusted to 7 by addition of a solution of NaHCO$_3$ and the layers separated. The aqueous phase was extracted with EtOAc (2×25 mL) and the combined organics were dried over MgSO$_4$, filtered and concentrated in vacuo. The crude material (28 mg) was purified by flash chromatography (Biotage SP4) with a gradient of EtOAc 30 to 60% in hexane. The isolated material (28 mg) was further purified by MDAP to afford 16 mg of the title compound (E16).

LC-MS: MH$^+$=227 (C$_{13}$H$_{10}$N$_2$O$_2$=226)

NMR ($\delta_H$), (d$_6$-DMSO): 6.51 (1H, d, J=7.4 Hz), 6.93 (2H, d, J=8.8 Hz), 7.06 (1H, J=8.5 Hz), 7.21 (1H, t, J=7.8 Hz), 7.47 (2H, d, J=8.8 Hz), 8.24 (1H, s), 9.8 (1H, bs), 10.38 (1H, bs).

Example 17

1-(3-Chloro-4-hydroxyphenyl)-1H-indazol-4-ol (E17)

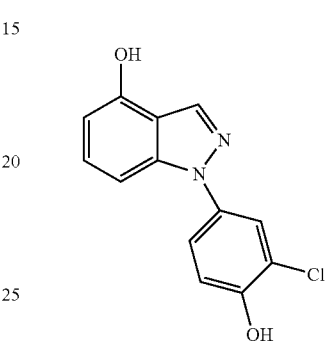

1-[3-Chloro-4-(methyloxy)phenyl]-4-[(phenylmethyl)oxy]-1H-indazole (D33) (460 mg, 1.26 mmol) was dissolved in dry DCM (15 mL) and degassed by sonication under a flow of argon. The solution was cooled to −78° C. and after 10 mins treated with BBr$_3$ (1M in DCM, 2.52 mL, 2.52 mmol) dropwise and when the addition was complete the bath was removed and it was allowed to reach room temperature still stirring under argon. After 17 hours the mixture was partitioned between DCM (50 mL)/water (50 mL), the pH adjusted to 7 by addition of a solution of NaHCO$_3$ and the layers separated. The aqueous phase was extracted with DCM (2×50 mL) twice and the combined organics were washed with brine (50 mL), separated and dried over MgSO$_4$. The crude material was purified by MDAP to afford 34 mg of the title compound (E17).

NMR ($\delta_H$), (d$_6$-DMSO): 6.53 (1H, d, 7.6 Hz), 7.11 (2H, m), 7.25 (1H, t, J=8 Hz), 7.49 (1H, dd, J=2.4, 8.4 Hz), 7.63 (1H, d, J=2.4 Hz), 8.27 (1H, s), 10.45 (2H, bs).

Example 18

1-(4-Hydroxy-3-methylphenyl)-1H-indazol-4-ol (E18)

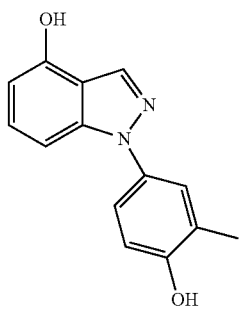

1-[3-Methyl-4-(methyloxy)phenyl]-4-[(phenylmethyl) oxy]-1H-indazole (D34) (550 mg, 1.64 mmol) was dissolved in dry DCM (20 mL) and degassed by sonication under a flow of argon. The solution was cooled to −78° C. and after 10 mins treated with BBr₃ (1M in DCM, 3.29 mL, 3.29 mmol) dropwise and when the addition was complete the bath was removed and it was allowed to reach room temperature. The reaction was followed by LC-MS. After 45 minutes more BBr₃ (1M in DCM, 3.29 mL, 3.29 mmol) was added to the mixture and after 17 hours it was partitioned between DCM (75 mL)/water (75 mL), the pH adjusted to 7 by addition of a solution of NaHCO₃ and the layers separated. The aqueous phase was extracted with DCM (2×50 mL) twice and the combined organics were washed with brine (50 mL) and dried over MgSO₄, filtered and concentrated in vacuo. The crude material (456 mg) was purified by flash chromatography (Biotage SP4) with a gradient of EtOAc 0 to 40% in hexane. The isolated material was further purified by MDAP to afford 36 mg of the title compound (E18).

LC-MS: MH⁺=241 ($C_{14}H_{12}N_2O_2$=240)

NMR ($\delta_H$), (d₆-DMSO): 2.21 (3H, s), 6.49 (1H, d, J=7.2 Hz), 6.94 (1H, d, J=8.4 Hz), 7.06 (1H, d, J=8.8 Hz), 7.21 (1H, t, J=7.6 Hz), 7.29 (1H, dd, J=2.8, 8.4 Hz), 7.37 (1H, d, J=2 Hz), 8.22 (1H, s), 9.63 (1H, bs), 10.3 (1H, bs).

Example 19

1-(3,5-Difluoro-4-hydroxyphenyl)-1H-indazol-4-ol (E19)

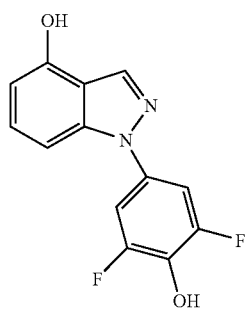

A solution of 1-{3,5-difluoro-4-[(phenylmethyl)oxy]phenyl}-4-[(phenylmethyl)oxy]-1H-indazole (D35) (257 mg, 0.58 mmol) in ethanol (10 mL) and ethyl acetate (10 mL) was hydrogenated in an H-cube over a 10% palladium on charcoal catalyst. The resulting solution was concentrated and then the crude product purified by silica gel chromatography eluting with 5-100% ethyl acetate in hexane to yield the title compound (E19) (126 mg).

LC-MS: MH⁺=263 ($C_{13}H_8F_2N_2O_2$=262)

Example 20

1-(3,5-Difluoro-4-hydroxyphenyl)-4-hydroxy-1H-indazole-6-carbonitrile (E20)

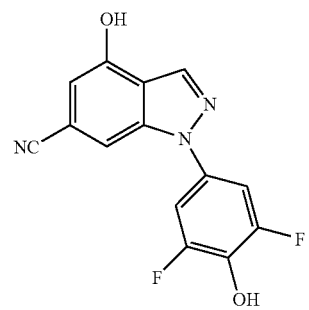

A solution of 1-{3,5-difluoro-4-[(phenylmethyl)oxy]phenyl}-4-hydroxy-1H-indazole-6-carbonitrile (D37) (610 mg, 1.617 mmol) in ethyl acetate (50 mL) was passed through the H-cube over a 10% palladium on charcoal catalyst at room temperature and pressure. The filtrate was concentrated and then triturated with dichloromethane and collected by filtration to yield the desired product (E20) (235 mg).

LC-MS: MH⁺=288 ($C_{14}H_7F_2N_3O_2$=287)

It is to be understood that the present invention covers all combinations of particular and preferred subgroups described herein above.

Assays for Determining Biological Activity

Assay Buffer (AB) (50 mM MOPES pH 7.5, 50 mM NaF, 2.5 mM CHAPs), in deionized water, 5 mM 1,4 dithiothreitol (DTT) added on day of the experiment. The appropriate amount of AB was placed in a plastic tube, adding solid DTT before the assay was run. AB with DTT was distributed to plastic tubes. We have found use of plastic to be important vs glass. A final concentration of 6 nM ERbeta protein was added to the tube followed by gentle inversion. A final concentration of 1.5 nM ER FP ligand (Fluormone™ EL Red 200 nM in 20 mM Tris, 90% Methanol purchased from Invitrogen catalogue no P3030) was added to the same tube followed by gentle inversion. This was allowed to sit for 5-10 minutes before adding it to the 384 assay plate. Similar protocol was used for ERalpha with a final concentration of 4 nM ERalpha and 1.5 nM ER FP ligand.

384 plates containing test compounds dissolved in 100% DMSO at 1 mM were serially diluted (1:3) by a Beckman FX. Serial diluted test compounds were added, 0.1 mL, to the assay plates with a maximum final concentration of 10 uM. Once the assay plates were ready, 10 uL of the above reagents were added to the appropriate set of plates with the Thermo combi. These plates were then sealed and place at room temperature for 3 hours.

The plates were then placed on the Molecular Devices Analyst and counted (excitation 535 nm, emission 590 nm with a 561 Dichroic mirror). Data was normalized to control then fitted to a non-linear least squares algorithm (see below).

pIC50 Calculation $$y=a+((b-a)/(1+(10^x/10^c)^d)$$

Results

The compound of Example 1, 3-11, 13-14 and 17 had a $pIC_{50}>7$ in the ER beta FP binding assay. The compound of Example 1 also had selectivity >10 fold versus ER alpha.

All compounds of the Examples had a $pIC_{50}>6$ in the ER beta FP binding assay.

The amino acid sequence of human ER beta used in this assay is

```
MKKHHHHHHG ELLLDALSPE QLVLTLLEAE PPHVLISRPS
APFTEASMMM SLTKLADKEL VHMISWAKKI PGFVELSLFD
QVRLLESCWM EVLMMGLMWR SIDHPGKLIF APDLVLDRDE
GKCVEGILEI FDMLLATTSR FRELKLQHKE YLCVKAMILL
NSSMYPLVTA TQDADSSRKL AHLLNAVTDA LVWVIAKSGI
SSQQQSMRLA NLLMLLSHVR HASNKGMEHL LNMKCKNVVP
VYDLLLEMLN AHVLRGCKSS ITGSECSPAE DSKSKEGSQN
PQSQ
```

The amino acid sequence of human ER alpha used in this assay is

```
MKKGHHHHHH GLVPRGSMIK RSKKNSLALS LTADQMVSAL
LDAEPPILYS EYDPTRPFSE ASMMGLLTNL ADRELVHMIN
WAKRVPGFVD LTLHDQVHLL ECAWLEILMI GLVWRSMEHP
GKLLFAPNLL LDRNQGKCVE GMVEIFDMLL ATSSRFRMMN
LQGEEFVCLK SIILLNSGVY TFLSSTLKSL EEKDHIHRVL
DKITDTLIHL MAKAGLTLQQ QHQRLAQLLL ILSHIRHMSN
KGMEHLYSMK CKNVVPLYDL LLEMLDAHRL HAPTS
```

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation the following claims.

What is claimed is:

1. A compound of formula (I):

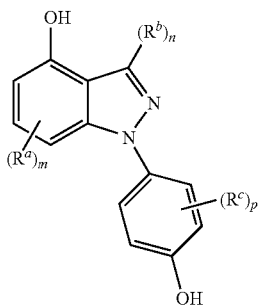

wherein $R^a$, $R^b$ and $R^c$ are independently selected from halo, $C_{1-4}$alkoxy, $C_{1-4}$alkyl, $C_{2-4}$alkenyl, $C_{1-5}$alkanoyl, $CF_3$, $CF_3O$ and cyano, provided that when one of the substitutents is attached to the C-5 of the indazole bicycle, this substituent $R^a$ is not a methoxy group;

m is zero or an integer from 1 to 3;

n is zero or 1;

p is zero or an integer from 1 to 4;

however m, n and p together equal 5 or less;

or a pharmaceutically acceptable salt thereof.

2. A compound according to claim 1 selected from:
1-(3-Fluoro-4-hydroxyphenyl)-1H-indazol-4-ol;
1-(3-Fluoro-4-hydroxyphenyl)-6-(methyloxy)-1H-indazol-4-ol1-(3-Fluoro-4-hydroxyphenyl)-4-hydroxy-1H-indazole-6-carbonitrile;
6-Fluoro-1-(3-fluoro-4-hydroxyphenyl)-1H-indazol-4-ol;
6-Bromo-1-(3-fluoro-4-hydroxyphenyl)-1H-indazol-4-ol;
6-Ethenyl-1-(3-fluoro-4-hydroxyphenyl)-1H-indazol-4-ol;
6-Ethyl-1-(3-fluoro-4-hydroxyphenyl)-1H-indazol-4-ol;
6-Chloro-1-(3-fluoro-4-hydroxyphenyl)-1H-indazol-4-ol;
1-(3-Fluoro-4-hydroxyphenyl)-6-methyl-1H-indazol-4-ol;
5-Fluoro-1-(3-fluoro-4-hydroxyphenyl)-1H-indazol-4-ol;
5-Bromo-1-(3-fluoro-4-hydroxyphenyl)-1H-indazol-4-ol;
5-Chloro-1-(3-fluoro-4-hydroxyphenyl)-1H-indazol-4-ol;
7-Fluoro-1-(3-fluoro-4-hydroxyphenyl)-1H-indazol-4-ol;
7-Chloro-1-(3-fluoro-4-hydroxyphenyl)-1H-indazol-4-ol;
1-(3-Fluoro-4-hydroxyphenyl)-3-methyl-1H-indazol-4-ol;
1-(4-Hydroxyphenyl)-1H-indazol-4-ol;
1-(3-Chloro-4-hydroxyphenyl)-1H-indazol-4-ol;
1-(4-hydroxy-3-methylphenyl)-1H-indazol-4-ol;
1-(3,5-Difluoro-4-hydroxyphenyl)-1H-indazol-4-ol; and
1-(3,5-Difluoro-4-hydroxyphenyl)-4-hydroxy-1H-indazole-6-carbonitrile; or a pharmaceutically acceptable salt thereof.

3. A pharmaceutical composition comprising a compound according to claim 1 or a pharmaceutically acceptable salt thereof together with a pharmaceutical carrier and/or excipient.

* * * * *